United States Patent
Ozaki et al.

(10) Patent No.: US 10,464,055 B2
(45) Date of Patent: *Nov. 5, 2019

(54) PHOTOCATALYTIC ELEMENT

(71) Applicant: NITTO DENKO CORPORATION, Osaka (JP)

(72) Inventors: Takashi Ozaki, Osaka (JP); Keita Mine, Osaka (JP); Guang Pan, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/124,296

(22) PCT Filed: Mar. 10, 2015

(86) PCT No.: PCT/JP2015/057605
§ 371 (c)(1),
(2) Date: Sep. 7, 2016

(87) PCT Pub. No.: WO2015/137511
PCT Pub. Date: Sep. 17, 2015

(65) Prior Publication Data
US 2017/0014815 A1  Jan. 19, 2017

Related U.S. Application Data

(60) Provisional application No. 61/950,982, filed on Mar. 11, 2014.

(30) Foreign Application Priority Data

May 30, 2014 (JP) ................................. 2014-113002

(51) Int. Cl.
*B01J 35/00* (2006.01)
*B01J 31/06* (2006.01)
(Continued)

(52) U.S. Cl.
CPC ............... *B01J 31/06* (2013.01); *B01J 23/30* (2013.01); *B01J 23/72* (2013.01); *B01J 23/835* (2013.01);
(Continued)

(58) Field of Classification Search
None
See application file for complete search history.

(56) References Cited

U.S. PATENT DOCUMENTS 5,897,958 A   4/1999 Yamada et al.
5,919,422 A   7/1999 Yamanaka et al.
(Continued)

FOREIGN PATENT DOCUMENTS

CN   201596150 U   10/2010
CN   101947439 A   1/2011
(Continued)

OTHER PUBLICATIONS

International Search Report of PCT/JP2015/057605, dated Jun. 9, 2015.
(Continued)

*Primary Examiner* — Yun Qian
(74) *Attorney, Agent, or Firm* — K&L Gates LLP; Louis C. Cullman; Hal Gibson

(57) ABSTRACT

In an embodiment, there is provided a photocatalyst element comprising: a porous resin base material that comprises interconnecting pores, and a three-dimensional network skeleton forming the pores; and a photocatalyst which is supported on a surface of the three-dimensional network skeleton of the porous resin base material and/or contained in the three-dimensional network skeleton of the porous resin base material. The photocatalyst element has excellent antimicrobial effects.

18 Claims, 7 Drawing Sheets

(51) Int. Cl.
  *B01J 31/28* (2006.01)
  *B01J 31/34* (2006.01)
  *B01J 35/02* (2006.01)
  *B01J 37/02* (2006.01)
  *B01J 37/03* (2006.01)
  *B01J 37/34* (2006.01)
  *B01J 23/30* (2006.01)
  *B01J 23/72* (2006.01)
  *B01J 23/835* (2006.01)
  *B01J 35/06* (2006.01)
  *B01J 37/04* (2006.01)
  *A61L 9/20* (2006.01)
  *A61L 2/08* (2006.01)
  *A61L 9/014* (2006.01)

(52) U.S. Cl.
  CPC ............ *B01J 31/28* (2013.01); *B01J 31/34* (2013.01); *B01J 35/004* (2013.01); *B01J 35/02* (2013.01); *B01J 35/06* (2013.01); *B01J 37/0219* (2013.01); *B01J 37/0232* (2013.01); *B01J 37/035* (2013.01); *B01J 37/04* (2013.01); *B01J 37/343* (2013.01); *A61L 2/088* (2013.01); *A61L 9/014* (2013.01); *A61L 9/205* (2013.01)

(56) References Cited

U.S. PATENT DOCUMENTS

| | | | |
|---|---|---|---|
| 6,228,480 B1 | 5/2001 | Kimura et al. | |
| 6,407,033 B1 | 6/2002 | Kimura et al. | |
| RE38,850 E | 10/2005 | Ikenaga et al. | |
| 7,510,595 B2 | 3/2009 | Freeman et al. | |
| 2003/0166466 A1* | 9/2003 | Hoke | B01D 53/02 502/439 |
| 2006/0223696 A1 | 10/2006 | Miyoshi et al. | |
| 2011/0192788 A1* | 8/2011 | Harada | B01D 69/12 210/500.38 |
| 2013/0180932 A1 | 7/2013 | Fukumura et al. | |

FOREIGN PATENT DOCUMENTS

| | | | |
|---|---|---|---|
| CN | 103301756 A | 9/2013 | |
| JP | A-H09-38191 | 2/1997 | |
| JP | 2006-015597 | 1/2006 | |
| JP | 2006-089323 A | 4/2006 | |
| JP | 2006-102709 A | 4/2006 | |
| JP | 2007-204581 A | 8/2007 | |
| JP | 2011-79713 | 4/2011 | |
| JP | 2012-030172 A | 2/2012 | |
| JP | 2012-167181 A | 9/2012 | |
| JP | 2013-209509 A | 10/2013 | |
| JP | 2013-212238 | 10/2013 | |
| KR | 10-2013-0132052 | * 12/2013 | ............. B01J 37/02 |
| WO | 2004/091785 A1 | 10/2004 | |
| WO | 2011/043496 A1 | 4/2011 | |
| WO | 2013/106776 A2 | 7/2013 | |

OTHER PUBLICATIONS

Office Action from Chinese Patent Office for Chinese App. No. 201580013055.9 (dated Jun. 25, 2018).

Office Action for Japanese Patent Application No. 2016-556904 dated May 7, 2019 (Original in Japanese, and translation in English provided).

Office Action for Chinese Patent Application No. 201580013055.9 dated Mar. 1, 2019 (Original in Chinese, and translation in English provided).

Sun et al., Advanced oxidizing technique in the environmental engineering. Beijing: Chemistry Engineering Press; Beijing: Environmental Science and Engineering Publishing Center, pp. 228-234 (2002). (Original in Chinese, and translation in English provided).

Gao et al., Nanobiomedicine. Beijing: Chemistry Engineering Press, pp. 305-307 (2007). (Original in Chinese, and translation in English provided).

Office Action for Japanese Patent Application No. 2016-556904 dated Nov. 27, 2018 (original and English translation provided).

* cited by examiner

Cu$_x$O-TiO$_2$ photo-catalyst

PHOTOCATALYTIC ELEMENT

CROSS REFERENCE TO RELATED APPLICATIONS

This application is a national phase of PCT/JP2015/057605 filed on 10 Mar. 2015 which claims priority to U.S. Provisional Patent Application No. 61/950,982 filed on 11 Mar. 2014, which also claims priority to JP Patent Application No. 2014-113002 filed on May 30, 2014, the entire disclosures of which are incorporated by reference.

TECHNICAL FIELD

The present invention relates to a photocatalytic element having adsorption for microorganisms floating in the air, and excellent antimicrobial effects in actual applications.

BACKGROUND ART

Photocatalysts have been used for various purposes, such as in antimicrobial, air refreshment, deodorization, and antifouling applications.

For example, visible light activated photocatalysts can be deployed for self-cleaning, air and water purification and many other interesting applications usually without any post-deployment non-renewable energy costs. This is because the photocatalysts are able to decompose pollutants (like dyes, volatile organic compounds and $NO_x$) using light available in the ambient like solar radiation or indoor and outdoor lighting. With the anticipated rapid adoption of UV-free indoor lighting (like LEDs and OLEDs), it is imperative to find ways to deploy visible-light activated photocatalysts in indoor applications for instance in cleaning room air in domestic, public and commercial spaces especially in confined areas like aircraft, public buildings, etc. Moreover, additional applications for antibacterial surfaces and self-cleaning materials can have wide applicability in the food service, transportation, health care and hospitality sectors.

For example, Patent Literature 1 discloses an antimicrobial deodorizing sheet that includes a sheet main body with an exposed titanium dioxide surface, and an adhesive layer laminated on the back surface of the sheet main body. Patent Literature 1 discloses that UV irradiation of the antimicrobial deodorizing sheet purifies air where the antimicrobial deodorizing sheet is attached, and weakens the activity of the surrounding microorganisms. The antimicrobial deodorizing sheet uses a silicone resin or a fluororesin as the constituting material of the base material sheet of the sheet main body.

In addition, various methods have been proposed to fix photocatalysts such as titanium oxide. See, for example, Patent Literatures 2 to 6. Thus there is a need for affixation of photocatalysts such as titanium oxide to substrate surfaces.

CITATION LIST

Patent Literature

PTL 1: JP-A-9-38191
PTL 2: U.S. Pat. No. 5,897,958
PTL 3: U.S. Pat. No. 6,228,480
PTL 4: U.S. Pat. No. 6,407,033
PTL 5: U.S. Pat. No. 7,510,595
PTL 6: Reissued U.S. Pat. No. RE38,850

SUMMARY OF INVENTION

Technical Problem

However, extensive studies by the present inventors found that the antimicrobial sheet described in Patent Literature 1 lacks adsorption for microorganisms floating in the air (hereinafter, also referred to as "airborne microbes"), and that the antimicrobial effects are not always sufficient in actual applications. Accordingly an object is to provide a photocatalytic element having adsorption for airborne microbes, and excellent antimicrobial effects in actual applications.

Solution to Problem

The present inventors conducted intensive studies, and found that the foregoing problems can be solved with a photocatalytic element that uses a porous resin base material (porous resin base material having a monolith structure) that comprises interconnecting pores and a three-dimensional network skeleton forming the pores. The present invention was completed on the basis of this finding.

Namely, the present invention relates to the following (1) to (20).

(1) A photocatalytic element comprising:
  a porous resin base material that comprises interconnecting pores, and a three-dimensional network skeleton forming the pores; and
  a photocatalyst which is supported on a surface of the three-dimensional network skeleton of the porous resin base material and/or contained in the three-dimensional network skeleton of the porous resin base material.

(2) The photocatalytic element according to (1) above, wherein the resin constituting the porous resin base material comprises at least one selected from the group consisting of a thermosetting resin, a thermoplastic resin, a ultraviolet curable resin, and an electron beam curable resin.

(3) The photocatalytic element according to (2) above, wherein the resin constituting the porous resin base material contains an epoxy resin.

(4) The photocatalytic element according to any one of (1) to (3) above, wherein the photocatalyst shows a visible light responsiveness.

(5) The photocatalytic element according to any one of (1) to (4) above, wherein a co-catalyst is further supported on the surface of the three-dimensional network skeleton of the porous resin base material and/or contained in the three-dimensional network skeleton of the porous resin base material.

(6) The photocatalytic element according to any one of (1) to (5) above, wherein a photocatalyst layer containing the photocatalyst, or a photocatalyst layer containing the photocatalyst and the co-catalyst is formed on the surface of the three-dimensional network skeleton of the porous resin base material.

(7) The photocatalytic element according to (5) or (6) above, wherein the photocatalyst contains titanium(IV) oxide or tin(IV) oxide, and the co-catalyst contains copper(I) oxide and/or copper(II) oxide, and wherein the co-catalyst is supported on the photocatalyst.

(8) The photocatalytic element according to (5) or (6) above, wherein the photocatalyst contains tungsten(VI) oxide, and the co-catalyst contains cerium(IV) oxide.

(9) The photocatalytic element according to any one of (1) to (8) above, wherein the photocatalyst, or the photocatalyst and the co-catalyst are supported on the surface of the three-dimensional network skeleton of the porous resin base material through an aerosol deposition method.

(10) The photocatalytic element according to any one of (1) to (9) above, wherein the photocatalytic element has a form of a sheet.

(11) A method for manufacturing the photocatalytic element according to (1), (2), (4), (5), (7), (8) or (10) above, which comprises:
dissolving a polymer in a first organic solvent to create a polymer precursor solution, wherein the polymer concentration is between 5% to about 40% by weight;
dispersing a photocatalytic material in a second organic solvent to create a photocatalytic material suspension;
mixing the polymer solution with the photocatalytic suspension to create a photocatalytic polymer suspension; and
submerging the photocatalytic polymer suspension in a third solvent, the polymer substantially insoluble in the third solvent at a temperature between about 10° C. to about 60° C., creating the photocatalytic element.

(12) The method according to (11) above, wherein the polymer is selected from polyethersulfone, polyacrylonitrile, polysulfone, and polypropylene.

(13) The method according to (11) or (12) above, wherein the first organic solvent is selected from the group consisting of N-methyl-2-pyrrolidone (NMP), dimethyl formamide (DMF), dimethylacetamide (DMAC), dimethyl sulfoxide (DMSO), tetrahydrofuran (THF) and chloroform.

(14) The method according to any one of (11) to (13) above, wherein the second organic solvent is selected from the group consisting of N-methyl-2-pyrrolidone (NMP), dimethyl formamide (DMF), dimethylacetamide (DMAC), dimethyl sulfoxide (DMSO), tetrahydrofuran (THF) and chloroform.

(15) The method according to any one of (11) to (14) above, wherein the first and second organic solvent are the same.

(16) The method according to any one of (11) to (15), further comprising casting the photocatalytic polymer suspension on a substrate surface.

(17) The method according to any one of (11) to (16), further comprising filtering the photocatalytic suspension.

(18) The method according to any one of (11) to (17), wherein the third solvent is water.

(19) The method according to any one of (11) to (18), wherein the photocatalytic element is a porous photocatalytic film.

(20) A photocatalytic element produced by the method according to any one of (11) to (19).

Advantageous Effects of Invention

The photocatalytic element according to the present invention includes a porous resin base material (porous resin base material having a monolith structure) that comprises interconnecting pores and a three-dimensional network skeleton forming the pores, and a photocatalyst supported on a surface of the three-dimensional network skeleton of the porous resin base material and/or contained in the three-dimensional network skeleton of the porous resin base material. Owing to the porous resin base material having a monolith structure used as the base material, the photocatalytic element of the present invention can exhibit adsorption for airborne microbes, and can efficiently and effectively decompose the adsorbed microbes with the photocatalytic activity of the photocatalyst. The photocatalytic element of the present invention thus has especially excellent antimicrobial effects in actual applications.

BRIEF DESCRIPTION OF DRAWINGS

FIGS. 6A to 6D show SEM surface images of a porous polyethersulfone (20%) membrane with 2 wt % photocatalyst ($Cu_xO/TiO_2$) loading in accordance with the second embodiment, wherein FIGS. 6A and 6B are top SEM surface images thereof, and FIGS. 6C and 6D are cross section SEM images thereof.

DESCRIPTION OF EMBODIMENTS

Figure 1:
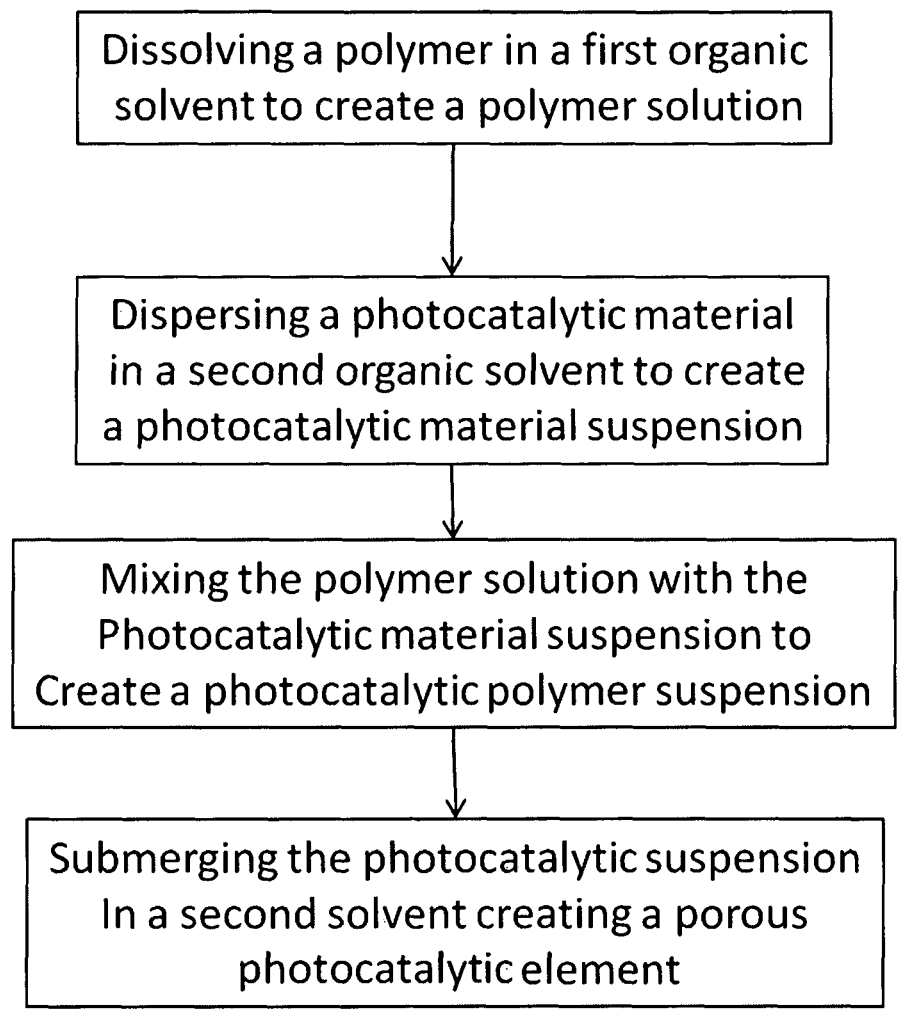
FIG. 1 is a schematic of an experimental in accordance with the second embodiment.
Figure 2:
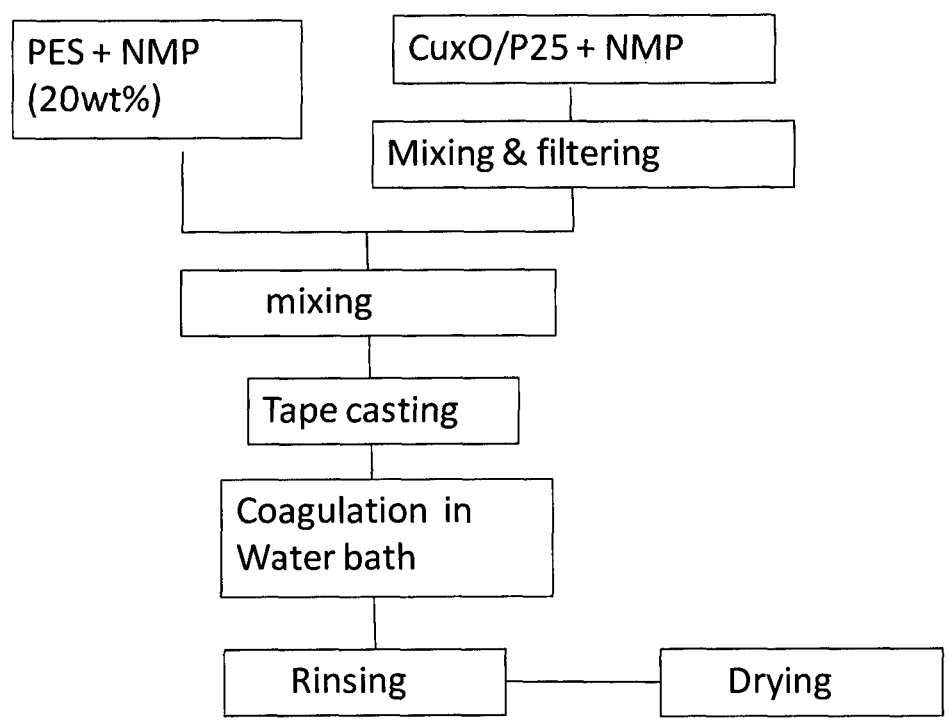
FIG. 2 is a schematic of an experimental in accordance with the second embodiment.

The photocatalytic element of the present invention includes a porous resin base material that comprises interconnecting pores and a three-dimensional network skeleton forming the pores, and a photocatalyst which is supported on a surface of the three-dimensional network skeleton of the porous resin base material and/or contained in the three-dimensional network skeleton of the porous resin base material. Herein, a photocatalytic element in which a photocatalyst is supported on a surface of the three-dimensional network skeleton of the porous resin base material may also be referred to as "photocatalyst support".

The shape of the photocatalytic element of the present invention is not particularly limited, and the photocatalytic element of the present invention may have various shapes, including, for example, a form of a thin film such as a sheet and a film, and various three dimensional shapes such as a sphere, a semi-sphere, a rectangle, a cube, a column, and a pyramid. Preferred for ease of production and handling are a sheet shape and a columnar shape, and a sheet shape is particularly preferred. In the following, a sheet-shaped photocatalytic element may be referred to as photocatalyst sheet.

(Photocatalyst and Co-Catalyst)

In the photocatalytic element of the present invention, the photocatalyst is supported on the surface of the three-dimensional network skeleton of the porous resin base material and/or contained in the three-dimensional network skeleton of the porous resin base material. As used herein, "photocatalyst (being) supported on the surface of the three-dimensional network skeleton of the porous resin base material" means that the photocatalyst directly or indirectly adheres to the surface of the three-dimensional network skeleton of the porous resin base material. In the following, "photocatalyst (being) supported on the surface of the three-dimensional network skeleton of the porous resin base material" may be expressed as "photocatalyst (being) supported on the porous resin base material." In addition, in the following, "photocatalyst (being) contained in the three-dimensional network skeleton of the porous resin base material" may be expressed as "photocatalyst (being) contained in the porous resin base material."

In the case where a photocatalyst is supported on the surface of the three-dimensional network skeleton of the porous resin base material, the photocatalyst may be supported only on a part of the surface of the three-dimensional network skeleton of the porous resin base material, or on the whole surface of the three-dimensional network skeleton. As used herein, the surface of the three-dimensional network skeleton of the porous resin base material includes a portion forming (defining) the external shape of the porous resin base material itself, and a portion forming (defining) the interconnecting pores.

In the photocatalytic element of the present invention, a co-catalyst may also be supported on the surface of the three-dimensional network skeleton of the porous resin base material and/or contained in the three-dimensional network skeleton of the porous resin base material, as desired, in addition to the photocatalyst. As with the case of the photocatalyst, "co-catalyst (being) supported on the surface of the three-dimensional network skeleton of the porous resin base material" means that the co-catalyst directly or indirectly adheres to the surface of the three-dimensional network skeleton of the porous resin base material. Likewise, "co-catalyst (being) supported on the surface of the three-dimensional network skeleton of the porous resin base material" may be expressed as "co-catalyst (being) supported on the porous resin base material." In addition, in the following, "co-catalyst (being) contained in the three-dimensional network skeleton of the porous resin base material" may be expressed as "co-catalyst (being) contained in the porous resin base material."

In the case where a co-catalyst is supported on the surface of the three-dimensional network skeleton of the porous resin base material, the co-catalyst may be supported only on a part of the surface of the three-dimensional network skeleton of the porous resin base material, or on the whole surface of the three-dimensional network skeleton.

In the present specification, photocatalyst and/or co-catalyst may also be referred to as "photocatalytic material".

In the present invention, the form of the photocatalyst supported on and/or contained in the porous resin base material is not particularly limited. For example, in the case of supporting the photocatalyst, the photocatalyst may be supported on the surface of the three-dimensional network skeleton of the porous resin base material in the form of a photocatalyst layer containing at least the photocatalyst. Alternatively, the photocatalyst may be supported in the form of a photocatalyst layer formed with an organic binder.

When the photocatalyst is supported on the porous resin base material in the form of a photocatalyst layer, the supported photocatalyst layer may contain other components such as a co-catalyst, in addition to the photocatalyst.

The following describes the photocatalyst supported on and/or contained in the porous resin base material, and the co-catalyst that may be supported on and/or contained in the porous resin base material as desired.

(Photocatalyst)

Photocatalysts are a substance that shows photocatalytic activity upon being irradiated with light of specific wavelengths (excitation light having a higher energy than the band gap between the valence and the conduction band of the photocatalyst). Since photocatalysts shows photocatalytic activity, they can exhibit a wide range of effects, including antimicrobial effect, air refreshment and deodorizing effect, and decomposition of harmful substances such as volatile organic compounds (VOCs).

Examples of the photocatalyst include metal oxides such as anatase-type or rutile-type titanium(IV) oxide ($TiO_2$), tungsten(III) oxide ($W_2O_3$), tungsten(IV) oxide ($WO_2$), tungsten(VI) oxide ($WO_3$), zinc oxide (ZnO), iron(III) oxide ($Fe_2O_3$), strontium titanate ($SrTiO_3$), bismuth(III) oxide ($Bi_2O_3$), bismuth vanadate ($BiVO_4$), tin(II) oxide (SnO), tin(IV) oxide ($SnO_2$), tin(VI) oxide ($SnO_3$), zirconium oxide ($ZrO_2$), cerium(II) oxide (CeO), cerium(IV) oxide ($CeO_2$), barium titanate ($BaTiO_3$), indium(III) oxide ($In_2O_3$), copper (I) oxide ($Cu_2O$), copper(II) oxide (CuO), potassium tantalate ($KTaO_3$), and potassium niobate ($KNbO_3$); metal sulfides such as cadmium sulfide (CdS), zinc sulfide (ZnS), and indium sulfide (InS); metal selenides such as cadmium selenate ($CdSeO_4$), and zinc selenide (ZnSe); and metal nitrides such as gallium nitride (GaN).

The photocatalysts exemplified above may be obtained by using methods, for example, such as solid-phase reaction, combustion synthesis, solvothermal synthesis, pyrolysis, and plasma synthesis. Preferably, the photocatalyst is obtained by using the radio frequency inductively coupled plasma (RF-ICP) technique. RF-ICP has high production efficiency, and can produce a high-purity photocatalyst. For example, the photocatalyst may be obtained under the RF-ICP conditions described in U.S. Pat. No. 8,003,563.

The activity of the photocatalyst can be improved by doping an element of certain species. Such an element may be called a "dopant", and examples of such dopants include alkali metals such as lithium (Li), sodium (Na), potassium (K), and cesium (Cs); alkali earth metals such as magnesium (Mg), calcium (Ca), strontium (Sr), and barium (Ba); noble metals such as gold (Au), platinum (Pt), rhodium (Rh), iridium (Ir), palladium (Pd), and ruthenium (Ru); transition metals such as iron (Fe), titanium (Ti), zinc (Zn), copper (Cu), tungsten (W), manganese (Mn), niobium (Nb), nickel (Ni), zirconium (Zr), and cerium (Ce); other metals such as tin (Sn), and aluminum (Al); metalloids such as boron (B), and arsenic (As); nonmetals such as nitrogen (N), carbon (C), sulfur (S), fluorine (F), and selenium (Se); and compounds containing such metals and nonmetals. In this specification, a photocatalyst doped with a dopant will be referred to as "doped-type photocatalyst".

The term "doping" means adding an arbitrarily chosen element (dopant) to the host compound crystals within a range that essentially does not change the basic crystalline structure of the photocatalyst. Whether the photocatalyst is doped or not can be confirmed by, for example, a peak shift in XPS (X-ray photoelectron spectroscopy). Methods used for forming the doped-type photocatalyst are not particularly limited, and may be, for example, a sol-gel method, a solid-phase reaction method, and an ion implantation method.

When the photocatalyst is a doped-type photocatalyst, the molar ratio of the host compound (compound subjected to doping) and the dopant in the photocatalyst is not particularly limited, and is preferably 99.9:0.1 to 80:20, more preferably 99.9:0.1 to 85:15, further preferably 99.9:0.1 to 87:13.

Preferably, the doped-type photocatalyst is doped with at least one selected from carbon (C), nitrogen (N), sulfur (S), fluorine (F), tin (Sn), zinc (Zn), manganese (Mn), aluminum (Al), selenium (Se), niobium (Nb), nickel (Ni), zirconium (Zr), cerium (Ce), and iron (Fe).

The photocatalyst may be a p-type or an n-type. A p-type photocatalyst may be obtained, for example, by doping a photocatalyst with high valance elements (for example, such as arsenic (As)). An n-type photocatalyst may be obtained, for example, by doping a photocatalyst with low valence elements (for example, such as boron (B)).

It is preferable that the photocatalyst contains a metallic compound (such as an oxide, a nitride oxide, an oxynitride carbide, or a halide), and more preferably contains a titanium compound, a tin compound, or a tungsten compound.

The average oxidation number or formal charge of titanium in the titanium compound is preferably +1 to +6, more preferably +2 to +4, further preferably +1 to +3. The average oxidation number or formal charge of tin in the tin compound is preferably +2 to +8, more preferably +1 to +6, further preferably +1 to +4. The average oxidation number or formal charge of tungsten in the tungsten compound is preferably +1 to +8, more preferably +1 to +6, further preferably +1 to +4.

More specifically, the photocatalyst preferably contains at least one selected from titanium(IV) oxide ($TiO_2$), tin(IV) oxide ($SnO_2$), tungsten(III) oxide ($W_2O_3$), tungsten(IV) oxide ($WO_2$), and tungsten(VI) oxide ($WO_3$). As the titanium(IV) oxide ($TiO_2$), an anatase-type titanium(IV) oxide ($TiO_2$) is preferred.

Incidentally, in the present specification, the phrase that "the photocatalyst contains (comprises) tungsten(VI) oxide ($WO_3$)" includes not only a case where the photocatalyst is a pure tungsten(VI) oxide ($WO_3$) but also a case where the photocatalyst contains a tungsten(VI) oxide ($WO_3$) doped with another element or compound. (The same applies to photocatalysts and co-catalysts other than tungsten oxide.)

Especially, it is preferable that the photocatalyst contains tungsten(VI) oxide ($WO_3$) because it makes it possible to form a photocatalyst layer that shows a sufficient photoactivity with visible light.

The photocatalyst preferably has a refractive index (R1) of 1.0 to 4.0, more preferably 1.0 to 3.0, particularly preferably 1.5 to 2.5 at a wavelength of 589 nm. With the photocatalyst refractive index (R1) falling in the range of 1.0 to 4.0, it becomes easier to reduce the refractive index difference from the co-catalyst, and thus becomes easier to form a translucent photocatalyst layer. Note that the refractive index values of the photocatalyst are measured values obtained with an Abbe refractometer according to the "Solid Sample Measurement Method" specified by JIS K 0062.

The shape of the photocatalyst is not particularly limited, but the photocatalyst is preferably particulate in shape. Many kinds of photocatalysts are poorly soluble in solvent. With the particulate shape, the photocatalyst can be dispersed in a dispersion medium to produce a dispersion liquid, which can then be used to easily form the photocatalyst layer by being coated and dried.

When the photocatalyst is particulate in shape, the average particle size of the photocatalyst is not particularly limited, and is preferably 5 nm to 1,000 nm, more preferably 5 nm to 100 nm, further preferably 5 nm to 30 nm. When the average particle size of the photocatalyst exceeds 1,000 nm, the overall surface area of the photocatalyst becomes smaller, and the photocatalyst may fail to sufficiently show photocatalytic activity. On the other hand, when the average particle size of the photocatalyst falls below 5 nm, particle aggregation tends to occur, and dispersibility may suffer.

Note that the average particle size of the photocatalyst is a volume-based 50% cumulative distribution diameter (D50) of photocatalyst particles dispersed in an arbitrary dispersion liquid as determined by dynamic light scattering frequency analysis (FFT-heterodyne method).

(Co-Catalyst)

Co-catalysts are a substance that accelerates the photocatalytic activity of the photocatalyst. According to the present invention, if desired, a co-catalyst may be supported on and/or contained in the porous resin base material in addition to the photocatalyst. The co-catalyst may be one that shows or does not show photocatalytic activity by itself.

In cooperation with the photocatalyst, the co-catalyst can increase the reaction rate of the photocatalyst by 1.2 fold or more, preferably 1.5 fold or more, further preferably 2.0 fold or more, particularly preferably 3.0 fold or more from that when the photocatalyst is used alone. The reaction rate of the photocatalyst may be based on, for example, the decomposition rate of acetaldehyde, a type of volatile organic compounds (VOCs).

Specifically, the photocatalyst, either alone or with the co-catalyst mixed with or supported by the photocatalyst, is put in a closed space charged with certain quantities of compressed air and acetaldehyde (calibration gas), and irradiated with visible light (wavelength 455 nm, irradiation intensity 200 mW/cm$^2$) for 1 hour. The acetaldehyde concentrations in the closed space before and after the irradiation are then compared to calculate the factor by which the reaction rate of the photocatalyst increased. For example, the acetaldehyde decomposition rate can be said to have increased 3 fold (a 3-fold increase of photocatalytic activity) when the acetaldehyde concentration in a closed space charged with the photocatalyst and the co-catalyst (either mixed with the photocatalyst or supported on the photocatalyst) becomes 20 ppm after the irradiation of the closed space containing 80 ppm of acetaldehyde (i.e., 60 ppm of acetaldehyde has decomposed) as compared to when the acetaldehyde concentration in a closed space charged with the photocatalyst alone becomes 60 ppm after the irradiation of the closed space containing 80 ppm of acetaldehyde (i.e., 20 ppm of acetaldehyde has decomposed).

Examples of the co-catalyst include copper(I) oxide ($Cu_2O$), copper(II) oxide (CuO), yttrium(III) oxide ($Y_2O_3$), molybdenum(VI) oxide ($MoO_3$), manganese(III) oxide ($Mn_2O_3$), gadolinium(III) oxide ($Gd_2O_3$), anatase-type or rutile-type titanium(IV) oxide ($TiO_2$), strontium titanate ($SrTiO_3$), potassium tantalate ($KTaO_3$), silicon carbide (SiC), potassium niobate ($KNbO_3$), silicon oxide ($SiO_2$), tin(IV) oxide ($SnO_2$), aluminum(III) oxide ($Al_2O_3$), zirconium oxide ($ZrO_2$), iron(III) oxide ($Fe_2O_3$), iron(II, III) oxide ($Fe_3O_4$), nickel(II) oxide (NiO), niobium(V) oxide ($Nb_2O_5$), indium oxide ($In_2O_5$), tantalum oxide ($Ta_2O_5$), cerium(II) oxide (CeO), cerium(IV) oxide ($CeO_2$), $A_rX_tO_s$ (where A is a rare earth element, X is an element other than rare earth elements, or a combination of elements other than rare earth elements, r is 1 to 2, t is 0 to 3, and s is 2 to 3), ammonium phosphomolybdate trihydrate (($NH_4$)$_3$[$PMo_{12}O_{40}$]), 12-tungstophosphoric acid ($PW_{12}O_{40}$), tungsten silicide ($H_4$[$SiW_{12}O_{40}$]), phosphomolybdic acid ($12MoO_3 \cdot H_3PO_4$), and cerium-zirconium composite oxide ($Ce_xZr_yO_2$) (y/x=0.001 to 0.999).

The co-catalyst may be supported on and/or contained in the porous resin base material in a state of simply mixed with the photocatalyst, or may be supported on and/or contained in the porous resin base material in a state of being supported on the photocatalyst. In this specification, a photocatalyst supporting the co-catalyst is referred to as "supporting-type photocatalyst". As used herein, the term "supporting" refers to the state where a substance different from the photocatalyst is adhering to the photocatalyst surface. Such an adhering state can be observed, for example, by scanning electron microscopy. Methods used for forming the supporting-type photocatalyst are not particularly limited, and may be, for example, an impregnation method, a photoreduction method, or sputtering. The supporting-type photocatalyst may be formed by using the method described in, for example, U.S. Patent Application Publication No. 2008/0241542. The co-catalyst may be doped with a dopant. A co-catalyst doped with a dopant will be referred to as doped-type co-catalyst. The compounds and elements used to dope the co-catalyst are as exemplified above in conjunction with the photocatalyst.

The co-catalyst preferably contains at least one selected from a cerium compound, a copper compound, a potassium compound, a strontium compound, a tantalum compound, a niobium compound, and a titanium compound. More preferably, the co-catalyst contains a cerium compound, or a copper compound. The average oxidation number or formal charge of the cerium compound is preferably +2 to +4. The average oxidation number or formal charge of the copper compound is preferably +1 to +2.

In one embodiment of the invention, the co-catalyst contains cerium oxide, more preferably cerium(IV) oxide ($CeO_2$). This embodiment is suited for use in decomposition of volatile organic compounds (VOCs). When the co-catalyst contains cerium(IV) oxide ($CeO_2$), it is preferable to dope the cerium(IV) oxide, preferably with tin (Sn). In the tin (Sn)-doped cerium(IV) oxide ($CeO_2$:Sn), the tin (Sn) accounts for preferably 1 mol % to 50 mol %, more preferably 1.5 mol % to 10 mol %, further preferably 1.5 mol % to 10 mol %, particularly preferably 1.5 mol % to 4.5 mol % of the total co-catalyst ($CeO_2$:Sn).

In another embodiment of the invention, the co-catalyst contains copper oxide, more preferably copper(I) oxide ($Cu_2O$) and/or copper(II) oxide (CuO). This emodiment is suited for anti-microbial applications. When the co-catalyst contains copper(I) oxide ($Cu_2O$) and/or copper(II) oxide (CuO), it is preferable that the copper(I) oxide ($Cu_2O$) and/or copper(II) oxide (CuO) are supported on the photocatalyst.

The shape of the co-catalyst is not particularly limited, but the co-catalyst is preferably particulate in shape for the same reasons described for the photocatalyst. When the co-catalyst is particulate in shape, the average particle size of the co-catalyst is not particularly limited, and is preferably 1 nm to 1,000 nm, more preferably 1 nm to 100 nm, further preferably 1 nm to 30 nm.

The co-catalyst has a refractive index (R2) of preferably 1.0 to 4.0, more preferably 1.0 to 3.0, particularly preferably 1.5 to 2.5 at 589 nm wavelength. With the co-catalyst refractive index (R2) falling in the range of 1.0 to 4.0, it becomes easier to reduce the refractive index difference from the photocatalyst, and form a desirably translucent photocatalyst layer.

Examples of the photocatalyst described above include a UV responsive photocatalyst that shows photocatalytic activity only with ultraviolet rays of less than 380 nm wavelength, and a visible-light responsive photocatalyst that shows photocatalytic activity also with visible light of 380 nm to 780 nm wavelengths. In the present invention, the photocatalyst may be a UV responsive photocatalyst or a visible-light responsive photocatalyst, and is preferably a visible-light responsive photocatalyst. The visible-light responsive photocatalyst shows some photoactivity with visible light even without the co-catalyst. The visible-light responsive photocatalyst, in cooperation with the co-catalyst, can thus show even higher photoactivity with visible light. When the photocatalyst is a visible-light responsive photocatalyst, the band gap is, for example, 1.5 eV to 3.5 eV, preferably 1.7 eV to 3.3 eV, more preferably 1.77 eV to 3.27 eV. Note that the photocatalyst may show a visible-light responsiveness in certain photocatalyst and co-catalyst combinations even when the photocatalyst is a UV responsive photocatalyst.

In the present invention, the photocatalyst is preferably one that shows a visible-light responsiveness. A visible-light responsive photocatalyst can show photocatalytic activity also with a visible-light emitting light source such as a fluorescence lamp and an LED, thereby exerting excellent antibacterial activity. Consequently, a photocatalytic sheet using a photocatalyst showing a visible-light responsivness can be used in a wider range of applications such as air purifier, building materials and refreshers.

Photocatalysts may be used either alone or as a mixture of two or more. When two or more photocatalysts are used as a mixture, one of the photocatalysts may function as the co-catalyst of the other photocatalyst. Co-catalysts may also be used alone or as a mixture of two or more.

In the case of forming a photocatalyst layer, it may contain other compounds (for example, such as a binder resin), in addition to the photocatalyst, or in addition to the photocatalyst and the co-catalyst. As is apparent, such additional compounds in the photocatalyst layer may involve a large refractive index difference from the photocatalyst or the co-catalyst, and sufficient translucency may not be ensured for the photocatalyst layer.

It is accordingly preferable that the photocatalyst layer is configured substantially solely from the photocatalyst, or from the photocatalyst and the co-catalyst. Photocatalyst layer being configured substantially solely from the photocatalyst, or from the photocatalyst and the co-catalyst, means that the photocatalyst, or the photocatalyst and the co-catalyst accounts for at least 80 mass %, preferably at least 90 mass % of the total photocatalyst layer.

In the case of carrying and/or incorporating the photocatalyst and the co-catalyst, the ratio (molar ratio) of the total photocatalyst and the total co-catalyst is preferably 99.5:0.5 to 16.7:83.3, more preferably 99.5:0.5 to 20:80, further preferably 99.5:0.5 to 50:50. Incidentally, same shall apply for the case of, for example, providing a photocatalyst layer containing the photocatalyst and the co-catalyst.

When the photocatalyst content is less than the lower limit of the foregoing ranges, the co-catalyst will be in excess of the photocatalyst amount, and the photocatalyst layer may fail to show sufficient photocatalytic activity. On the other hand, when the photocatalyst content exceeds the upper limit of the foregoing ranges, the co-catalyst will be deficient relative to the photocatalyst amount, and the photocatalyst layer may fail to show sufficient photocatalytic activity.

When the photocatalyst layer contains the photocatalyst and the co-catalyst, the absolute value of the difference between the photocatalyst refractive index (R1) and the co-catalyst refractive index (R2) at 589 nm wavelength (|R1-R2|) is preferably 0 to 0.35, more preferably 0 to 0.30, further preferably 0 to 0.20, particularly preferably 0 to 0.16. Note that |R1−R2|=0 means that the photocatalyst refractive index (R1) and the co-catalyst refractive index (R2) are the same.

With the refractive index difference of the photocatalyst and the co-catalyst falling in the foregoing ranges, light more easily passes through the photocatalyst layer than being refracted therein (the photocatalyst layer will have increased translucency). This makes it possible to form a photocatalyst layer having superior translucency.

In the present invention, in the case of carrying and/or incorporating the photocatalyst and the co-catalyst, the combination of the photocatalyst and the co-catalyst contained in the photocatalyst layer is not particularly limited.

In a preferred embodiment, the photocatalyst contains titanium(IV) oxide ($TiO_2$) or tin(IV) oxide ($SnO_2$), and the co-catalyst contains copper(I) oxide ($Cu_2O$) and/or copper (II) oxide (CuO). In this case, the co-catalyst containing copper(I) oxide ($Cu_2O$) and/or copper(II) oxide (CuO) is preferably supported on the photocatalyst containing titanium(IV) oxide ($TiO_2$) or tin(IV) oxide ($SnO_2$). Excellent visible-light responsiveness and photocatalytic activity, and also particularly excellent anti-microbial properties can be exerted by using titanium(IV) oxide ($TiO_2$) or tin(IV) oxide ($SnO_2$) as the photocatalyst, and copper(I) oxide ($Cu_2O$) and/or copper(II) oxide (CuO) as the co-catalyst. In this specification, a co-catalyst-supporting type photocatalyst supporting a co-catalyst $Cu_xO$ on a photocatalyst $TiO_2$ may be represented by $Cu_xO$—$TiO_2$. Similarly, a co-catalyst-supporting type photocatalyst supporting a co-catalyst $Cu_xO$ on a photocatalyst $SnO_2$ may be represented by $Cu_xO$—$SnO_2$. Here, "$Cu_xO$" is intended to mean a state where two types of copper oxides, CuO (X=1; copper(II) oxide) and $Cu_2O$ (X=2; copper(I) oxide) are present.

In another preferred embodiment, the photocatalyst contains tungsten(VI) oxide ($WO_3$), and the co-catalyst contains cerium(IV) oxide ($CeO_2$). Excellent visible-light responsiveness and photocatalytic activity, and also particularly excellent ability to decompose volatile organic compounds (VOCs) can be exerted by using tungsten(VI) oxide ($WO_3$) as the photocatalyst, and cerium(IV) oxide ($CeO_2$) as the co-catalyst.

When forming the photocatalyst layer, the thickness of the photocatalyst layer is not particularly limited. As is evident, adherence to microbes may suffer when the photocatalyst layer is too thick. On the other hand, the photocatalyst layer may fail to show sufficient photocatalytic activity when the photocatalyst layer is too thin.

Considering these, the thickness of the photocatalyst layer is preferably 0.1 μm to 20 μm, more preferably 0.1 μm to 10 μm, particularly preferably 0.1 μm to 5 μm.

The visible light transmittance of the photocatalyst layer is preferably 70% or more, more preferably 80% or more, particularly preferably 90% or more. The transmittance of the photocatalyst layer for light having a wavelength of 589 nm is preferably 80% or more, more preferably 90% or more.

The visible light transmittance value is a measured value according to JIS R 3106.

In some embodiments, the photocatalytic material can be an oxide comprising an element that can be titanium, tungsten, tantalum, tin, zinc or strontium oxide. In some embodiments, the oxide can be doped or undoped, loaded or unloaded. In some embodiments, the oxide can have a valence band deeper than that of the copper loaded materials valence bands. In some embodiments, the photocatalytic material can be a plural phase composite of photocatalytic materials. In some embodiments, the photocatalytic material can be ananatase, rutile, wurtzite, spinel, perovskite, pyrocholore, garnet, zircon and/or tialite phase material or mixtures thereof. Each of these options is given its ordinary meaning as understood by one having ordinary skill in the semiconductor art. Comparison of an X-ray diffraction pattern of a given standard and the produced sample is one of a number of methods that may be used to determine whether the sample comprises a particular phase. Exemplary standards include those XRD spectra provided by the National Institute of Standards and Technology (NIST) (Gaitherburg, Md., USA) and/or the International Centre for Diffraction Data (ICDD, formerly the Joint Committee on Powder Diffraction Standards [JCPDS]) (Newtown Square, Pa., USA).

In some embodiments, the plural phase photocatalytic materials comprise anatase phase and rutile phase compounds. In some embodiments, the plural phase photocatalytic materials can be titanium oxides. In some embodiments, the anatase phase can be 2.5% to about 97.5%, 5% to about 95%, and/or about 10% to about 90%; and the rutile phase can be 97.5% to about 2.5%, 95% to about 5%, and/or about 90% to about 10%. A non-limiting example of a suitable material includes, but is not limited to a $TiO_2$ mixture sold under the brand name P25 (83% Anataste $TiO_2$+17% Rutile $TiO_2$) sold by Evonik (Parissipany, N.J., USA)).

In some embodiments, the photocatalytic material can be a $Cu_xO$ loaded photocatalytic composite as described in U.S. patent application Ser. No. 13/840,859, filed Mar. 15, 2013; and/or U.S. Provisional Application 61/835,399, filed Jun. 14, 2013; and U.S. patent application Ser. No. 13/741,191, filed Jan. 14, 2013 (U.S. Publication No. 2013/0192976, published Aug. 1, 2013). In some embodiments, the photocatalytic material can be selected from $Cu_xO$ loaded P25 and/or $Cu_xO$ loaded Ti:Sn(C,N,O)$_2$.

(Porous Resin Base Material)

The porous resin base material in the present invention comprises interconnecting pores, and a three-dimensional network skeleton forming the pores. Specifically, the porous resin base material in the present invention has a monolith structure. As used herein, "monolith structure" refers to a co-continuous structure integrally configured from a continuous three-dimensional network skeleton and interconnecting pores.

The shape of the porous resin base material is not particularly limited, and may be appropriately selected according to the required shape of the photocatalytic element. In the following, a sheet-like porous resin base material may be referred to as "porous sheet".

First Embodiment

The followings describe an embodiment (first embodiment) of the photocatalytic element.

In the first embodiment of the photocatalytic element, examples of the resins constituting the porous resin base material include thermosetting resins, thermoplastic resins, ultraviolet curable resins, and electron beam curable resins. These may be used either alone or in a combination of two or more. Thermosetting resins are preferred for their properties such as compatibility, and curability.

The size of the porous resin base material is not particularly limited, as long as the present invention remains effective, and may be appropriately selected according to the environment for which the photocatalytic element is intended. For example, when the porous base material has a form of a sheet, the thickness of the porous resin base material is not particularly limited, and is preferably 500 μm or less, more preferably 300 μm or less in terms of ease of handling. On the other hand, the thickness thereof is preferably 1 μm or more, more preferably 5 μm or more because strength suffers when the porous base material is too thin.

The average pore size of the porous resin base material is not particularly limited, and is preferably 500 nm or less, more preferably 300 nm or less because an excessively large average pore size lowers strength. On the other hand, the average pore size is preferably 20 nm or more, more preferably 40 nm or more because adherence to microbes weakens when the average pore size is too small. The average pore size is not particularly limited in itself, and may be, for example, an average pore size measured by using a mercury intrusion technique.

In view of adherence to microbes, the porosity of the porous resin base material is preferably 30 to 80%, more preferably 40 to 60%.

The method for producing the porous resin base material is not particularly limited. As an example, the following describes using a thermosetting resin for the production of a sheet-like porous resin base material (porous sheet).

First, a resin mixture containing a thermosetting resin and a curing agent is prepared into a cylindrical or columnar cured resin, and the cured resin is cut (by rotary cutting) into a predetermined thickness from surface, thereby forming a resin sheet.

The thermosetting resin usable herein is not limited, as long as it can form a cured resin with a curing agent. Examples include epoxy resins, phenolic resins, melamine resins, urea-formaldehyde resins (urea resins), alkyd resins, unsaturated polyester resins, polyurethane, thermosetting polyimide, silicone resins, and diallyl phthalate resins. For obtaining a homogeneous porous material, it is preferable to use thermosetting resins that can form a porous sheet with a curing agent and a porogen. Specifically, epoxy resins may preferably be used.

The cylindrical or columnar cured resin may be produced, for example, by charging the resin mixture into a cylindrical or columnar mold (molding container), and promoting a curing reaction by allowing time to stand. Here, the mixture may be heated or stirred, as required. For uniform curing, this is preferably followed by allowing the mixture to stand in a 10 to 35° C. atmosphere. When producing a cylindrical cured resin, a cylindrical cured resin may be produced by punching the center of a columnar cured resin produced by using a columnar mold.

The cylindrical or columnar mold (molding container) used for the injection of the resin mixture may be a material as may be appropriately selected from, for example, metal, glass, curable clay, curable plastic, and a combination of these. Preferably, the cylindrical or columnar mold is an anti-corrosive metal mold such as aluminum and stainless steel that has had a silicon-based release agent applied thereto and dried thereon.

The size of the cylindrical or columnar cured resin is not particularly limited, and the thickness from the central axis of the cylindrical cured resin is preferably 5 cm or more, more preferably 10 cm or more in terms of the production efficiency of the resin sheet. The diameter of the cylindrical or columnar cured resin is not particularly limited either, and is preferably 30 cm or more in terms of the production efficiency of the resin sheet, and is more preferably 40 to 150 cm in terms of uniform curing. The width (the length along the axial direction) of the cured resin may be appropriately set taking into account the intended size of the resin sheet. The width is typically 20 to 200 cm, and is preferably 30 to 150 cm, more preferably 50 to 120 cm for ease of handling.

The cylindrical or columnar cured resin is then cut into a long resin sheet of a predetermined thickness by cutting the surface being rotated about the cylinder or column axis. The line speed for cutting the cylindrical or columnar cured resin is, for example, about 2 to 50 m/min.

Preferably, the thickness of the cut resin sheet is set taking into account an about 8 to 15% reduction that occurs after the porogen removing step and drying step as described later.

The followings describes in detail a preferred embodiment of the porous resin base material, which is a case where an epoxy resin is used as an example of the thermosetting resin.

Examples of the epoxy resins include polyphenyl based epoxy resins such as bisphenol A epoxy resin, brominated bisphenol A epoxy resin, bisphenol F epoxy resin, bisphenol AD epoxy resin, stilbene epoxy resin, biphenyl epoxy resin, bisphenol A novolac epoxy resin, cresol novolac epoxy resin, diaminodiphenylmethane epoxy resin, and tetrakis (hydroxyphenyl)ethane based resin; aromatic epoxy resins such as fluorene-containing epoxy resin, triglycidyl isocyanurate, and heteroaromatic ring (for example, triazine ring)-containing epoxy resin; and non-aromatic epoxy resins such as aliphatic glycidyl ether epoxy resin, aliphatic glycidyl ester epoxy resin, alicyclic glycidyl ether epoxy resin, and alicyclic glycidyl ester epoxy resin. These may be use either alone or in a combination of two or more.

In order to ensure chemical resistance and film strength, and to form a porous sheet having a uniform three-dimensional network skeleton and uniform pores, it is preferable to use at least one aromatic epoxy resin selected from the group consisting of bisphenol A epoxy resin, brominated bisphenol A epoxy resin, bisphenol F epoxy resin, bisphenol AD epoxy resin, fluorene-containing epoxy resin, and triglycidyl isocyanurate, or at least one alicyclic epoxy resin selected from the group consisting of alicyclic glycidyl ether epoxy resin, and alicyclic glycidyl ester epoxy resin. It is particularly preferable to use at least one aromatic epoxy resin that has an epoxy equivalent of 6,000 or less and a melting point of 170° C. or less, specifically at least one selected from the group consisting of bisphenol A epoxy resin, brominated bisphenol A epoxy resin, bisphenol AD epoxy resin, fluorene-containing epoxy resin, and triglycidyl isocyanurate, or at least one alicyclic epoxy resin that has an epoxy equivalent of 6,000 or less and a melting point of 170° C. or less, specifically at least one selected from the group consisting of alicyclic glycidyl ether epoxy resin, and alicyclic glycidyl ester epoxy resin.

Examples of the curing agent include aromatic curing agents such as aromatic amines (for example, m-phenylenediamine, diaminodiphenylmethane, diaminodiphenylsulfone, benzyldimethylamine, and dimethylaminomethylbenzene), aromatic acid anhydrides (for example, phthalic anhydride, trimellitic anhydride, and pyromellitic anhydride), phenolic resins, phenol novolac resins, heteroaromatic ring-containing amines (for example, triazine ring-containing amine); and non-aromatic curing agents such as aliphatic amines (for example, ethylenediamine, diethylenetriamine, triethylenetetramine, tetraethylenepentamine, iminobispropylamine, bis(hexamethylene)triamine, 1,3,6-trisaminomethylhexane, polymethylenediamine, trimethylhexamethylenediamine, and polyetherdiamine), alicyclic amines (isophoronediamine, menthanediamine, N-aminoethylpiperazine, 3,9-bis(3-aminopropyl)2,4,8,10-tetraoxaspiro(5,5)undecane adduct, bis(4-amino-3-methylcyclohexyl)methane, bis(4-aminocyclohexyl)methane, and modified products of these), and aliphatic polyamideamines of polyamines and dimer acids. These may be used either alone or in a combination of two or more.

In order to form a uniform three-dimensional network skeleton and uniform pores, and to ensure film strength and elastic modulus, it is preferable to use at least one aromatic amine curing agent that has two or more primary amines within the molecule, specifically at least one selected from the group consisting of m-phenylenediamine, diaminodiphenylmethane, and diaminodiphenylsulfone, or at least one alicyclic amine curing agent that has two or more primary amines within the molecule, specifically at least one selected from the group consisting of bis(4-amino-3-methylcyclohexyl)methane, and bis(4-aminocyclohexyl)methane.

Preferred as the combination of the epoxy resin and the curing agent are a combination of an aromatic epoxy resin and an alicyclic amine curing agent, and a combination of an alicyclic epoxy resin and an aromatic amine curing agent.

These are preferred as the porous base material of the photocatalytic element because it increases the heat resistance of the epoxy resin sheet.

The epoxy resin and the curing agent may be used with a porogen to produce the porous sheet. As used herein, porogen is a solvent that is capable of dissolving the epoxy resin and the curing agent, and that is capable of causing a reaction-induced phase separation after the polymerization of the epoxy resin and the curing agent. Examples of porogens include cellosolves such as methyl cellosolve, and ethyl cellosolve; esters such as ethylene glycol monomethyl ether acetate, and propylene glycol monomethyl ether acetate; glycols such as polyethylene glycol, and polypropylene glycol; and ethers such as polyoxyethylene monomethyl ether, and polyoxyethylene dimethyl ether. These may be used either alone or in a combination of two or more.

In order to form a uniform three-dimensional network skeleton and uniform pores, it is preferable to use methyl cellosolve, ethyl cellosolve, polyethylene glycols with molecular weights of 600 or less, ethylene glycol monomethyl ether acetate, propylene glycol monomethyl ether acetate, polypropylene glycol, polyoxyethylene monomethyl ether, and polyoxyethylene dimethyl ether, particularly preferably polyethylene glycols with molecular weights of 200 or less, polypropylene glycols with molecular weights of 500 or less, polyoxyethylene monomethyl ether, and propylene glycol monomethyl ether acetate. These may be used either alone or in a combination of two or more.

The porogen may be a solvent that may not dissolve or may poorly dissolve the individual epoxy resin and curing agent at ordinary temperature, but dissolves the reaction product of the epoxy resin and the curing agent. Examples of such porogens include brominated bisphenol A epoxy resin (Epicoat 5058, manufactured by Japan Epoxy Resin).

The properties of the epoxy resin porous sheet, including porosity, average pore size, and pore size distribution depend on the type and the mixing ratio of the raw materials such as epoxy resin, curing agent and porogen, and reaction conditions such as the heating temperature and the heating time for the reaction-induced phase separation. It is therefore preferable to choose optimum conditions by creating a phase diagram of the system for obtaining the desired porosity, average pore size, and pore size distribution. The co-continuous structure of the crosslinked epoxy resin and the porogen can be fixed in a specific state, and a stable pore structure can be obtained by controlling, for example, the molecular weight, the molecular weight distribution, the system viscosity, and the crosslinking reaction rate of the crosslinked epoxy resin undergoing a phase separation. In view of adherence to microbes, the porosity of the epoxy resin porous sheet is preferably 30 to 80%, more preferably 40 to 60%.

Preferably, the types of the epoxy resin and the curing agent, and the mixing proportions of these components are decided so that the proportion of the carbon atoms deriving from the aromatic rings ranges from 0.1 to 0.65 with respect to the total carbon atoms constituting the epoxy resin porous sheet. The stability of the cured product tends to suffer when the proportion is below 0.1. Above 0.65, it becomes difficult to form a uniform three-dimensional network skeleton.

The mixing proportion of the curing agent with respect to the epoxy resin is preferably 0.6 to 1.5 in terms of an equivalent of the curing agent with respect to 1 equivalent of the epoxy group. The crosslink density of the cured product tends to decrease when the curing agent equivalent is less than 0.6, and properties such as heat resistance and solvent resistance tend to decrease. Above 1.5, the unreacted curing agent tends to remain as residues, and inhibit improvements of crosslink density. In this embodiment, a curing promoting agent may be added to the solution to obtain the desired pore structure, in addition to the curing agent. Known curing promoting agents may be used, for example, such as tertiary amines (e.g., triethylamine, and tributylamine), and imidazoles (e.g., 2-phenol-4-methylimidazole, 2-ethyl-4-methylimidazole, and 2-phenol-4,5dihydroxyimidazole).

The average pore size of the epoxy resin porous sheet may be adjusted within the desired range by appropriately adjusting conditions such as the proportions of the total epoxy equivalent and the porogen, and the cure temperature. The average pore size can easily be adjusted by adjusting the mixing proportion of the porogen. In order to make an average pore size about 20 to 500 nm, it is preferable to use the porogen in 30 to 90 weight % with respect to the total weight of the epoxy resin, the curing agent, and the porogen. When the porogen amount is less than 30 weight %, the average pore size tends to become excessively small, and pore formation tends to fail. On the other hand, the average pore size tends to become excessively large when the porogen amount exceeds 90 weight %. It is also preferable to mix and use two or more epoxy resins of different epoxy equivalents. In this case, the epoxy equivalent difference is preferably 100 or more, and a liquid epoxy resin and a solid epoxy resin are preferably used as a mixture at ordinary temperature.

The curing temperature and the curing time of the epoxy resin composition depend on the types of the epoxy resin and the curing agent. Typically, the curing temperature is about 15 to 150° C., and the curing time is about 10 minutes to 72 hours. For uniform pore formation, the epoxy resin composition is cured preferably at room temperature, preferably at an initial curing temperature of about 20 to 40° C., for 1 to 48 hours. The curing may be followed by post-curing (post-treatment) to increase the degree of crosslinking of the crosslinked epoxy resin. Post-cure conditions are not particularly limited, and post-curing may be performed at room temperature or at a temperature of about 50 to 160° C. for about 2 to 48 hours.

The porogen is then removed from the epoxy resin sheet to form an epoxy resin porous sheet having interconnecting pores. The solvent used to remove the porogen from the epoxy resin sheet may be, for example, water, DMF (N,N-dimethylformamide), DMSO (dimethylsulfoxide), THF (tetrahydrofuran), or a mixed solvent of these, and may be appropriately selected according to the type of the porogen. Supercritical fluids such as water and carbon dioxide also may be preferably used.

The epoxy resin porous sheet may be dried after removing the porogen. The drying conditions are not particularly limited, and the epoxy porous sheet is dried at a temperature of typically about 40 to 120° C., preferably about 50 to 80° C., for about 3 minutes to 3 hours.

The foregoing described using a thermosetting resin (specifically, epoxy resin) for the production of the sheet-like porous resin base material (porous sheet). However, the technique also can be appropriately used in applications in which resins other than thermosetting resins are used, and/or a porous resin base material of a shape other than a sheet shape is produced.

Examples of the thermoplastic resins include natural rubber, butyl rubber, isoprene rubber, chloroprene rubber, an ethylene-vinyl acetate copolymer, an ethylene-acrylic acid copolymer, an ethylene-acrylic acid ester copolymer, polybutadiene resins, polycarbonate resins, thermoplastic polyimide resins, and polyamide resins (e.g., 6-nylon, and 6,6- nylon), phenoxy resins, acrylic resins, saturated polyester resins (e.g., PET (polyethylene terephthalate), and PBT (polybutylene terephthalate)), polyamideimide resins, and fluororesins.

One possible way of forming the porous resin base material with the thermoplastic resin is, for example, dissolving a supercritical fluid in the resin, and then removing the fluid to obtain a foam.

Examples of the ultraviolet curable resins include epoxy acrylate resins, and urethane acrylate resins.

Examples of the electron beam curable resins include polyester acrylate resins.

One possible way of forming the porous resin base material with ultraviolet curable resins or electron beam curable resins is, for example, employing a photo-induced phase separation method.

Some embodiments of a production process of the photocatalytic element of the first embodiment is described below.

In an embodiment, the photocatalytic element of the first embodiment may be produced by supporting the photocatalyst on the porous resin base material.

The method used to support the photocatalyst is not particularly limited, and the photocatalyst may be formed by using, for example, dry deposition methods such as aerosol deposition method (also referred to as AD method, or gas deposition method), high velocity oxygen fuel (HVOF) spraying, cold spraying, atomic layer deposition (ALD), chemical vapor deposition (CVD), and physical vapor deposition (PVD), and wet deposition methods such as spin coating and dip coating. The aerosol deposition method is particularly preferred for its ability to provide excellent photocatalytic activity for the supported photocatalyst, and excellent adhesion for the porous resin base material.

These methods also can be used when supporting the co-catalyst with the photocatalyst. For example, the foregoing methods may be used to support a mixture of the photocatalyst and the co-catalyst on the porous resin base material.

Furthermore, in an embodiment, a photocatalytic element in which a photocatalyst and/or a co-catalyst is/are contained in the three-dimensional network skeleton of the porous resin base material can be produced by incorporating the photocatalyst and/or the co-catalyst into the resin material for constituting the porous resin base material and then forming the porous resin base material in a manner as described above. Moreover, a photocatalyst and/or a co-catalyst may further be supported on the three-dimensional network skeleton of the porous resin base material containing a photocatalyst and/or a co-catalyst.

Second Embodiment

The followings describe another embodiment (second embodiment) of the photocatalytic element. A method for manufacturing the photocatalytic element is provided in the second embodiment.

The photocatalytic element made in accordance with the second embodiment, including a film and/or a tubular member, can provide photocatalytic effects and maintain improved durability and photocatalytic activity lifetime.

In some embodiments, as shown in FIG. 1, a method for manufacturing a photocatalytic element is described. In some embodiments, the element can be a film. In some embodiments, the element can be a tubular member. In some embodiments, the method comprises dissolving a polymer in a first organic solvent to create a polymer solution, wherein the polymer concentration is between 5% to about 40% by weight; dispersing a photo-catalytic material in a second organic solvent to create a photocatalytic material suspension; mixing the polymer solution with the photocatalytic suspension to create a photocatalytic polymer suspension; and submerging the photocatalytic polymer suspension in a third solvent, the polymer substantially insoluble in the third solvent at a temperature between about 10° C. to about 60° C., creating a porous photocatalytic element. In some embodiments, the polymer precursor can be selected from polyethersulfone, polyacrylonitrile, polysulfone, and polypropylene. In some embodiments, the first organic solvent can be N-methyl-2-pyrrolidone (NMP), dimethyl formamide (DMF), dimethylacetamide (DMAC), dimethyl sulfoxide (DMSO), tetrahydrofuran (THF) and/or chloroform. In some embodiments, the second organic solvent can be selected from NMP, DMF, DMAC, DMSO, THF, and/or chloroform. In some embodiments, the first and second organic solvent can be the same solvent. In some embodiments, the method can further comprise casting the photocatalytic polymer suspension on a substrate surface. In some embodiments, the method can further comprise filtering the photocatalytic suspension. In some embodiments, the third solvent can be water. In some embodiments, a photocatalytic film is described, the film can be made as described above. See also FIG. 3.

In some embodiments, the polymer can be a thermoplastic polymer. In some embodiments, the polymer can be polyethersulfone, polyacrylonitrile, polysulfone and/or polypropylene.

In some embodiments, the first or second organic solvent [s] can be a dipolar aprotic solvent. In some embodiments, the organic solvent can be NMP, DMF, DMAC, DMSO, THF and/or chloroform. In some embodiments, the organic solvent is capable of dissolving 5% by weight or more of resin at a temperature of 60° C. In some embodiments, the same organic solvent can be used to dissolve the polymer to create a polymer solution and suspend the photo-catalytic material to create a photocatalytic material suspension. In some embodiments, different organic solvents can be used to dissolve the polymer and suspend the photo-catalytic material.

In some embodiments, the polymer solution comprises a polymer concentration between 1% to about 50% by weight. In some embodiments, the polymer solution can comprise an organic solvent described above. In some embodiments, the polymer concentration can be between 5%, 10%, and/or 15% to about 15%, 30%, and/or about 40% by weight. In some embodiments, the polymer concentration can be between any of the aforedescribed lower limits, e.g., 10% to any of the aforedescribed upper limits, e.g., about 30% by weight. In some embodiments, the polymer solution has a viscosity of between 1,000 to 100,000 mPa*s, between 25,000 to 75,000 mPa*s, and/or about 50,000 mPa*s.

In some embodiments, the method comprises dispersing a photo-catalytic material in a second organic solvent to create a photocatalytic material suspension.

In some embodiments, the photocatalytic element can be a film. In some embodiments, e.g., when the element is a film, the PCat/binder material can be applied to a substrate. In some embodiments, the substrate can be a material that is resistive to the organic solvent[s]. In some embodiments, the substrate can be a material that is insoluble to the organic solvent[s]. In some embodiments, the substrate can be glass, metal, and/or ceramic. In some embodiments, the substrate can be glass.

In some embodiments, applying the mixture to a substrate further comprises spin-coating the binder-PCat material solution on the substrate at about 500 revolutions per sec (rps) to about 3000 rps for between about 5 seconds to about 30 seconds. In one embodiment, the spin coating can be about 1200 rps for about 20 sec.

In some embodiments, applying the mixture to a substrate further comprises casting the suspension mixture upon the substrate. A suitable casting procedure can be described in U.S. Pat. No. 8,283,843, issued Oct. 9, 2012, which is incorporated by reference in its entirety. In some embodiments, the blade gap can be between 0.5 mil to about 50 mils, between about 2.0 mils to about 35 mils, or between about 3.5 mils to about 20 mils. In some embodiments, the photocatalytic polymer suspension can be formed by applying the photocatalytic polymer suspension on substrates by wire wound lab rod with wire size in the range of 0.003 to 0.020 inches (Paul N. Gardner Inc.).

In some embodiments, applying the mixture to a substrate further comprises tape casting the mixture upon the substrate. In some embodiments, the blade gap can be between 0.5 mil to about 50 mils, between about 2.0 mils to about 35 mils, or between about 3.5 mils to about 20 mils.

In some embodiments, the photocatalytic material/polymer solution or mixture can be submerged in a third solvent, the polymer being substantially insoluble in the third solvent. In some embodiments, the third solvent is incapable of dissolving 5% by weight or more of the polymer at a temperature of 60° C. In some embodiments, less than 5%, less than 3%, less than 1%, less than 0.1% by weight of the polymer can dissolve in the third solvent. In some embodiments, the third solvent can be water, hexane, pentane, benzene, toluene, methanol, ethanol, carbon tetrachloride, o-dichlorobenzene, trichloroethylene, ethylene glycol, diethylene glycol, triethylene glycol, propylene glycol, butylene glycol, pentanediol, hexanediol, aliphatic hydrocarbons such as low-molecular-weight polyethylene glycols, aromatic hydrocarbons, aliphatic polyhydric alcohols, aromatic polyhydric alcohols, chlorinated hydrocarbons, other chlorinated organic liquids, and their mixtures. In some embodiments, the third solvent can be water.

In some embodiments, the previously submerged photocatalytic material/polymer mixture, having been solidified, e.g., a film, can be rinsed after having been submerged in the third solvent. In some embodiments, the film can be rinsed in the same third solvent. In some embodiments, the film can be rinsed by submerging the film in a new batch of third solvent. In some embodiments, the film can be rinsed at least 3 hours, at least 5 hours, at least 8 hours, at least 10 hours, at least 12 hours and/or at least 15 hours.

In some embodiments, when the film is applied to a substrate surface, the film may be removed from the substrate surface. In some embodiments, a release layer can be interposed between the substrate surface and the film.

In some embodiments, a plurality of photocatalytic nanomaterials can be disposed on a surface of a substrate. In some embodiments, the plurality of photocatalytic nanomaterials may have a total mass of about 1 ng to about 500 ng, about 10 ng to about 100 ng, or about 20 ng to about 60 ng for each $cm^2$ of area of the surface of the light-emitting layer.

In some embodiments, the nominal thickness of a plurality of photocatalytic materials measured by the Quartz Crystal microbalance, which measures the mass deposited onto it, can be about 0.0001 nm to about 2 nm or about 0.001 nm to about 0.75 nm. In some embodiments, the photocatalytic coating comprises a binder matrix and a photocatalytic material. In some embodiments, the photocatalytic coating can be a discontinuous layer defining apertures or voids between islands of photocatalytic material.

In some embodiments, the porous element can be in the form of a porous film. In some embodiments, the porous element can be in the form of a porous tubular member.

If the porous membrane is formed in a hollow fiber, after a polymer solution is prepared, the polymer solution and a lumen forming fluid are respectively discharged from the external pipe and the internal pipe of a double co-extrusion head for spinning hollow fiber membranes, while being submerged or solidified in a cool bath. Thus, a hollow fiber membrane is formed. In this instance, a gas or a liquid may be used as the lumen forming fluid. However, in some embodiments, the same liquid as the cooling liquid is preferably used, which contains 60 to 100 percent of a poor solvent, e.g., water. In this instance, by varying the compositions of the lumen forming fluid and the cooling liquid in the cool bath, a hollow fiber membrane having the three-dimensional network structure can be provided. The lumen forming fluid may be supplied with cooling. However, if the cool bath has sufficient power to solidify the hollow fiber membrane, the lumen forming fluid may be supplied without cooling.

If the porous membrane is formed in a flat membrane, after a resin solution is prepared, the polymer solution can be discharged from a slit extrusion head and solidified in a cool bath. In this instance, by adjusting the compositions of cooling liquids coming into contact with one surface of the flat membrane and with the other surface, or by bringing the cool bath into contact with only one surface of the flat membrane, the resulting flat membrane can have both a three-dimensional network structure and a spherical structure. The method for varying the cooling liquid compositions coming into contact with one surface of the flat membrane and with the other surface is not particularly limited. However, for example, a cooling liquid is sprayed from one side of the flat membrane and another cooling liquid is sprayed from the other side. The method for bringing only one side of the flat membrane into contact with a cool bath is not particularly limited. However, for example, the flat membrane may be floated on the surface of the cool bath, or a cooling liquid may be sprayed from only one side of the flat membrane.

Figure 3:
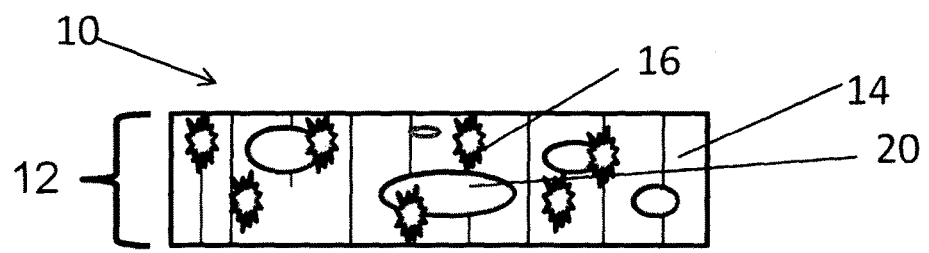
FIG. 3 is a schematic of an embodiment in accordance with the second embodiment.

In some embodiments, as shown in FIG. 3, porous film 10 can have a wall element 12. In some embodiments, wall element 12 has a plurality of pores 20 defined within a polymer matrix 14. A plurality of photocatalytic particles 16 can be disposed within matrix 14. In some embodiments, the pores can be generally circular (spherical) or elliptical, e.g., a pocket type, on the order of 0.01 microns to about 10 microns in diameter.

Figure 4:
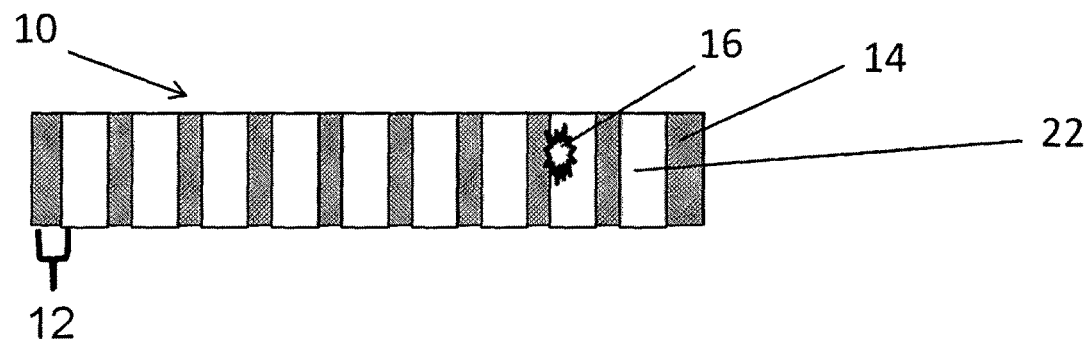
FIG. 4 is a schematic of an embodiment in accordance with the second embodiment.
Figure 7:
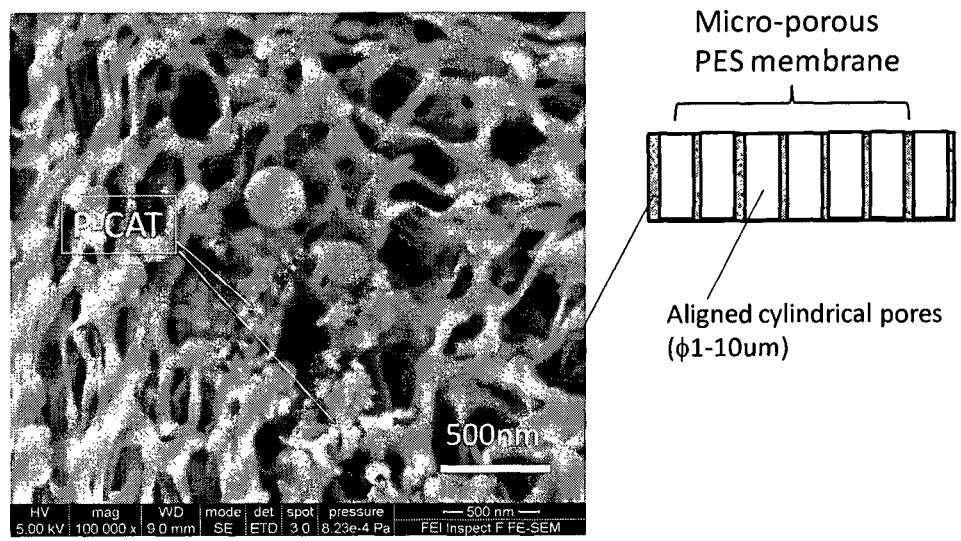
FIG. 7 is an SEM image of a porous wall of porous polyethersulfone(20%) membrane with 2 wt % photocatalyst ($Cu_xO/TiO_2$) loading in accordance with the second embodiment.

In some embodiments, as shown in FIG. 4, the porous photocatalytic element, e.g., a film 10, has a plurality of pores 20 defined within a polymer matrix 14. In some embodiments, the porous film 10 has a substantially greater x (width), and y (length) dimension relative the z (depth) dimension. In this embodiment, the pores can have a generally tubular or elongated form, in some cases extending from one side completely to the other side and/or extending from one side a substantial distance into the film, but not completely there through. In some embodiments, the pores can extend substantially perpendicular to the surface of the element. In some embodiments, the pores can be generally cylindrical. In some embodiments, the pores can be finger type pores. See FIGS. 6A, 6B, 6C, and 6D. A plurality of photocatalytic particles 16 can be disposed within matrix 14. In some embodiments the pores can be pocket-type pores, for example, generally circular (spherical) or elliptical, on the order of 0.01 nanometers to about 500 nanometers in diameter. See FIG. 7.

In some embodiments, as shown in FIG. 4, porous film 10 can have a plurality of pores 22 defined by wall 12, the wall comprising a polymer matrix 14. In this embodiment, pores 22 can be finger-like, for example have a generally tubular or elongated form, in some cases extending from one side completely to the other side and/or extending from one side a substantial distance into the film, but not completely there through. A plurality of photocatalytic particles 16 can be disposed within matrix 14.

Figure 5:
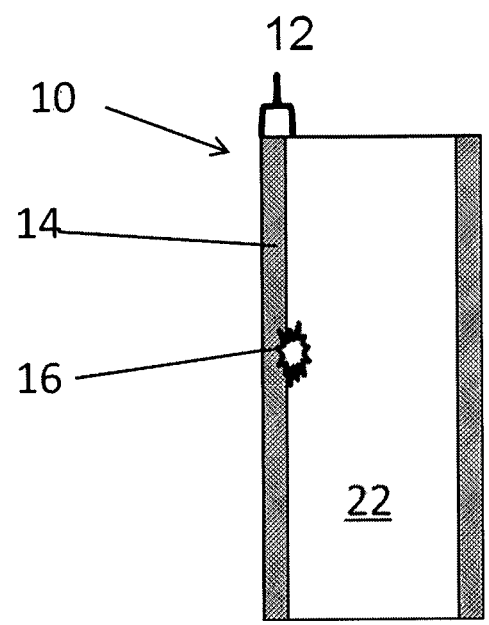
FIG. 5 is a schematic of an embodiment in accordance with the second embodiment.
Figure 6:
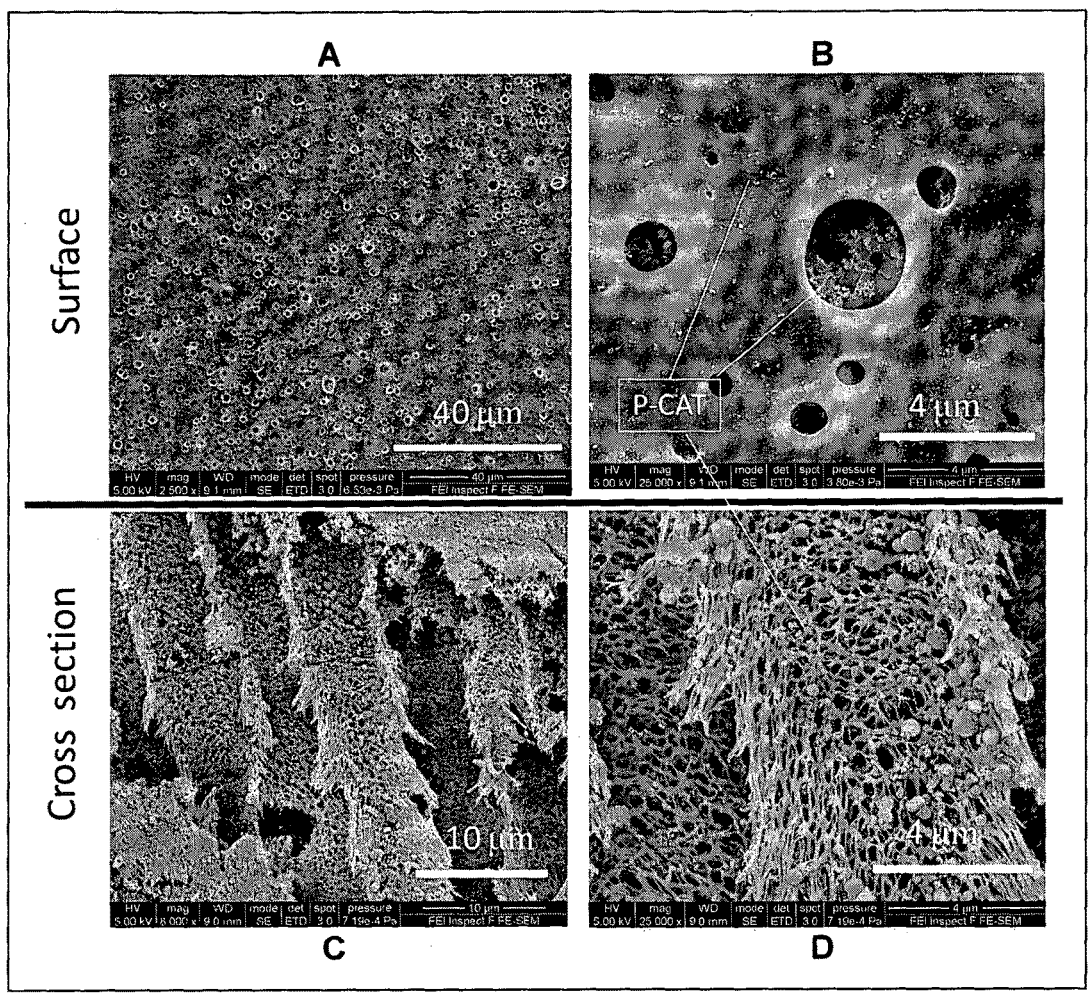

In some embodiments, as shown in FIG. 5, the porous element 10 has a generally tubular configuration. In some embodiments, the porous element 10 can be in the form of a generally u-shaped tube. In some embodiments, the tubular porous element can have walls 12 defining finger type pores 22. In some embodiments, the walls of the tubular member can be similar to that described with respect to FIG. 3 and/or FIG. 4.

The pocket type mean pore size of the three-dimensional network structure is preferably in the range of 5 nm to 1 micron, and more preferably in the range of 10 nm to 500 nm. See FIG. 7. The finger type pore can have a mean pore size of the three-dimensional network structure can be in the range of about 0.1 microns to 50 microns, in the range of 1 microns to 10 microns. See FIGS. 6C and 6D. The mean pore size of the three-dimensional network structure refers to the mean diameter of the pores in the three-dimensional network structure. In order to determine the mean pore size, the cross section of the porous membrane is photographed through a scanning electron microscope (SEM) or the like at a magnification allowing the pores to be clearly observed, and the diameters of arbitrary 10 or more pores, preferably arbitrary 20 or more pores, are measured and number-averaged. Also, the mean pore size may be determined using an image processing system in which the mean diameter of the pores is measured. In this instance, the mean diameter of equivalent rounds is defined as the mean pore size. The mean diameter of equivalent rounds is determined by the expression (a plus b)0.5, wherein a and b are the breadth and the length of elliptical pores, respectively.

The photocatalytic element of the present invention may further include elements other than the porous resin base material and the photocatalyst as needed, provided that such addition does not interfere with the objects of the present invention. For example, the photocatalyst may be directly supported on the porous resin base material, or via some other layer such as a photocatalyst protective layer, and a microbe adsorption layer.

The photocatalytic element of the present invention may further include a layer, for example, such as an adhesive layer, on its surface. For example, a photocatalyst sheet may be formed that further includes an adhesive layer on the surface of a sheet-like porous resin base material (porous sheet) opposite the photocatalyst supporting surface. In an embodiment further provided with an adhesive layer (for example, the photocatalyst sheet with an adhesive layer), the photocatalytic element may be used by attaching the adhesive layer to various different places as may be decided according to the intended use of the photocatalytic element of the present invention. For example, the photocatalytic element may be used in many different applications by attaching the adhesive layer to a range of materials from products such as instruments, devices, containers, wrapping, and members to surfaces such as walls, floors, and ceilings in environments where the photocatalytic element is used or intended.

The adhesive constituting the adhesive layer used in the present embodiment is not particularly limited, and known adhesives such as acrylic adhesives, rubber adhesives, silicone adhesives, and urethane adhesives may be appropriately used. In the present embodiment, it is preferable to protect the adhesive layer with a release liner or the like until the adhesive layer is actually used to attach the photocatalytic element to objects such as above.

One or more layers in the photocatalytic element of the present invention may be subjected to various treatments such as a deodorant treatment, an anti-microbial treatment, and a color treatment as may be decided according to the properties desired in different applications of the photocatalytic element. For the deodorant treatment of the porous resin base material, for example, a deodorant compound may be attached to or may impregnate the surface of the porous resin base material via a polymer, or a deodorant compound may be mixed with the raw material of the porous resin base material, and this mixture may be used to produce the porous resin base material. The porous resin base material can retain the deodorant compound after these procedures. The porous resin base material also can retain an anti-microbial agent after an anti-microbial treatment performed by using the same technique. The porous resin base material also may be subjected to a color treatment with a colorant. These and other treatments also may be performed for layers (for example, other layers such as above) other than the porous resin base material by using the same technique.

For improved adsorption for microbes, the photocatalytic element of the present invention may support adsorbents such as activated carbon, and zeolite.

The photocatalytic element of the present invention may include more than one porous resin base material, provided that it does not interfere with the objects of the present invention.

The photocatalytic element of the present invention includes the porous resin base material having a monolith structure, and thus can adsorb airborne microbes to its surface. The adsorbed microbes are efficiently and effectively decomposed by the photocatalytic activity exhibited by the photocatalyst on the photocatalytic element.

The photocatalytic element of the present invention configured as above thus has excellent antimicrobial effects.

With the excellent antimicrobial effects, the photocatalytic element of the present invention can be used as an antimicrobial material in a variety of applications where antimicrobial effects are desired.

For example, mold prevention is needed in the cultivation, distribution, or preservation of plants such as fruits, vegetables, cereals, and flowers, and in the distribution and preservation of fresh food products (such as fruit and vegetables, cereals, dressed meat, and fish), various processed foods, and food and beverages such as drinks. The photocatalytic element of the present invention, when used near objects of interest such as plants and food and beverages, can effectively prevent mold generation with its excellent antimicrobial effects produced by photoirradiation. The photocatalytic element of the present invention is particularly useful for objects susceptible to mold generation, for example, such as strawberries, tomatoes, and oranges.

In this case, the photocatalytic element of the present invention may be placed in direct contact with the object, or with a distance from the object, as long as the antimicrobial effects of the present invention are effectively exhibited.

The photocatalytic element of the present invention also can exhibit its excellent antimicrobial effects in places where antimicrobial effects are desired, for example, such as in bath rooms, lavatories, and toilets.

The photocatalytic element of the present invention can exhibit not only antimicrobial effects but air refreshing and deodorizing effects with its photocatalytic activity. The photocatalytic element of the present invention thus also has use in applications where air refreshing and deodorizing effects are needed, for example.

EXAMPLES

The present invention is described below in greater detail using examples. Note, however, that the present invention is not limited by the following examples.

Example 1

Two types of bisphenol A epoxy resins (jER 827: 9.9 kg and jER 1009: 4.2 kg; Mitsubishi Chemical Corporation), 3.1 kg of bis(4-aminocyclohexyl)methane, and 34.9 kg of polyethylene glycol (PEG 200, Sanyo Chemical Industries, Ltd.) were charged into a 50-liter SUS cylindrical container after applying a release agent inside the container. These were mixed and stirred, and cured at room temperature (23° C.) for half a day (12 hours) to obtain an epoxy resin cured body. The cured body was then cut into a sheet of about a 100 μm thickness with a cutting lathe, and was dried after removing the polyethylene glycol in purified water, thereby obtaining an epoxy resin porous sheet having a thickness of 88 μm and an average pore size of 270 nm. The epoxy resin porous sheet was then cut into an epoxy resin porous sheet measuring 15 cm in length and 10 cm in width (thickness 88 μm, average pore size 270 nm). This epoxy resin porous sheet was used as the porous resin base material of a photocatalytic element (photocatalyst sheet), as follows.

The epoxy resin porous sheet was installed on the seat of a substrate holder in the deposition chamber (22° C.) of an aerosol deposition device (carrier gas: oxygen gas).

Here, a 20-mm distance was provided between the jet orifice of the deposition nozzle and the surface of the epoxy resin porous sheet.

Separately, 25 g of a $TiO_2$ powder (photocatalyst, average particle diameter: 0.03 μm, Nippon Aerosil Co., Ltd.) and 250 ml of ion exchange water were put in a 500-ml eggplant flask, and stirred at room temperature to uniformly disperse the particles, thereby preparing an aqueous dispersion of $TiO_2$ powder.

Then, 0.68 g of copper(II) chloride dihydrate (Wako Pure Chemical Industries, Ltd.) was dissolved in 5 ml of ion exchange water, and the aqueous solution of copper(II) chloride was added to the aqueous dispersion of $TiO_2$ powder. Subsequently, it was stirred for 1 hour while being heated at 90° C., thereby preparing liquid A.

Then, an aqueous solution of sodium hydroxide prepared by dissolving 1.255 g of sodium hydroxide in 25 ml of ion exchange water was added to the liquid A, and then the pH of the solution was increased from 3 to 11, thereby preparing liquid B.

Then, an aqueous solution of glucose prepared by dissolving 6.275 g of glucose (Wako Pure Chemical Industries, Ltd.) in 37.5 ml of ion exchange water was added to the liquid B. It was further stirred for 1 hour while being heated at 90° C., whereby particles of copper(I) oxide and copper (II) oxide were precipitated on the surfaces of the particles of titanium oxide.

Next, the particles after the reaction were filtrated, then subjected to sufficient water washing, and the particles were dried at 100° C. Consequently, $Cu_xO$-supporting $TiO_2$ powder (co-catalyst-supporting type photocatalyst) was produced. According to the result of ICP analysis, it was confirmed that 1.0 part by weight of particles of copper oxide were supported with respect to 100 parts by weight of particles of titanium oxide.

Thirty grams of the $Cu_xO$-supporting $TiO_2$ powder (co-catalyst-supporting type photocatalyst) was charged into a 500-mL glass aerosol chamber.

Thereafter, with the gas pipe on-off valve closed, and the connecting tube on-off valve open, the mechanical booster pump and the rotary pump were driven to create a reduced pressure of 50 Pa inside the deposition chamber and the aerosol chamber.

After adjusting the oxygen gas flow rate to 7 L/min with a gas flowmeter, the gas pipe on-off valve was opened while vibrating the aerosol chamber with a shaker. This aerosolized the $Cu_xO$-supporting $TiO_2$ powder inside the aerosol chamber, and the aerosol thus obtained was expelled through the deposition nozzle.

Incidentally, the pressure inside the aerosol chamber was about 50,000 Pa, and the pressure inside the deposition chamber was about 280 Pa. The temperature inside the deposition chamber was 25° C.

The aerosol through the deposition nozzle was blown onto the surface of the epoxy resin porous sheet while moving the fixed epoxy resin porous sheet on the seat at a speed (relative speed) of 4 mm/s in x-y directions by moving the stage of the substrate holder.

This procedure was repeated to laminate a photocatalyst layer of 1 μm thickness on the surface of the epoxy resin porous sheet. Consequently, the photocatalytic element (photocatalyst sheet) of Example 1 was prepared. Scanning electron microscopy confirmed that the $Cu_xO$ particles (co-catalyst) were supported on the $TiO_2$ particles (photocatalyst) in the photocatalyst layer in the photocatalytic element (photocatalyst sheet) of Example 1.

Example 2

In Example 2, a $Cu_xO$ supporting $SnO_2$ powder was produced in the same manner as in Example 1, except that an $SnO_2$ powder (photocatalyst, average particle size 0.015 μm, Kanto Kagaku) was used in place of the $TiO_2$ powder. An ICP analysis of the powder confirmed that 1.0 weight part of copper oxide particles were supported with respect to 100 weight parts of tin oxide. Thereafter, a photocatalytic element (photocatalyst sheet) of Example 2 was produced in the same manner as in Example 1, except that the $Cu_xO$ supporting $SnO_2$ powder was used in place of the $Cu_xO$ supporting $TiO_2$ powder. Scanning electron microscopy confirmed that the $Cu_xO$ particles (co-catalyst) were supported on the $SnO_2$ particles (photocatalyst) in the photocatalyst layer in the photocatalytic element (photocatalyst sheet) of Example 2.

Example 3

In Example 3, a photocatalytic element (photocatalyst sheet) was produced in the same manner as in Example 1, except that a mixture of 15 g of a $WO_3$ powder (photocatalyst, average particle size 0.25 Kojundo Chemical Laboratory Co., Ltd.) and 15 g of a CeO$_2$ powder (co-catalyst, average particle size 0.025 μm, Sigma Aldrich JAPAN) was used in place of the C$_x$O supporting TiO$_2$ powder used in Example 1.

Example 4

In Example 4, a photocatalytic element (photocatalyst sheet) was produced in the same manner as in Example 1, except that 30 g of a WO$_3$ powder (photocatalyst, average particle size 0.25 Kojundo Chemical Laboratory Co., Ltd.) was used in place of the Cu$_x$O supporting TiO$_2$ powder used in Example 1.

Comparative Example 1

In Comparative Example 1, a photocatalytic element (photocatalyst sheet) was produced in the same manner as in Example 1, except that a PET sheet (length 15 cm×width 10 cm×thickness 100 μm, Toray) was used in place of the epoxy resin porous sheet of a monolith structure produced in Example 1.
(Evaluation of Antimicrobial Effects)

The antimicrobial effects of the photocatalytic elements (photocatalyst sheets) of Examples and Comparative Example were evaluated as follows.

The photocatalyst sheet (length 15 cm×width 10 cm) was installed on the bottom surface of a 3-L transparent container (length 15 cm×width 20 cm×height 10 cm). Five strawberries were then placed on the photocatalyst sheet at regular intervals. The container was sealed, and irradiated with fluorescent light (illuminance: 1,000 Lx) for 1 week at room temperature (23° C.). After one week, the strawberry surface was visually inspected for the presence or absence of a mold. The results are presented in Table 1.

TABLE 1

| | Presence or absence of mold on strawberry surface |
|---|---|
| Example 1 | Generation of mold was not observed |
| Example 2 | Generation of mold was not observed |
| Example 3 | Generation of mold was not observed |
| Example 4 | Generation of mold was not observed |
| Comparative Example 1 | Generation of mold was observed |

As shown in Table 1, a mold was not observed on the surfaces of the strawberries placed on the photocatalyst sheets of Examples 1 to 4. The result indicates that the photocatalyst sheets of Examples 1 to 4 have excellent antimicrobial effects. The effects of the photocatalyst sheets of Examples 1 to 4 are believed to be due to the epoxy resin porous sheet of a monolith structure adsorbing the airborne microbes in the container, and effectively decomposing the adsorbed microbes with the photocatalytic activity of the photocatalyst.

On the other hand, the photocatalyst sheet of Comparative Example 1 failed to prevent mold generation on strawberry surfaces. Presumably, this is because of the lack of the monolith structure in the PET sheet used in the photocatalyst sheet of Comparative Example 1, and the inability of the photocatalyst sheet to adsorb the airborne microbes inside the container, and sufficiently decompose the airborne microbes with the photocatalytic activity of the photocatalyst.

Example 5

25 g of a TiO$_2$ powder (trade name: SUPER-TITANIA, grade: G-1, average particle diameter: 0.25 Showa Denko K. K.) and 250 ml of ion exchange water were put in a 500-ml eggplant flask, and stirred at room temperature to uniformly disperse the particles, thereby preparing an aqueous dispersion of TiO$_2$ powder.

Then, 0.68 g of copper(II) chloride dihydrate (Wako Pure Chemical Industries, Ltd.) was dissolved in 5 ml of ion exchange water, and the aqueous solution of copper(II) chloride was added to the aqueous dispersion of TiO$_2$ powder. Subsequently, it was stirred for 1 hour while being heated at 90° C., thereby preparing liquid A.

Then, an aqueous solution of sodium hydroxide prepared by dissolving 1.255 g of sodium hydroxide in 25 ml of ion exchange water was added to the liquid A, and then the pH of the solution was increased from 3 to 11, thereby preparing liquid B.

Then, an aqueous solution of glucose prepared by dissolving 6.275 g of glucose (Wako Pure Chemical Industries, Ltd.) in 37.5 ml of ion exchange water was added to the liquid B. It was further stirred for 1 hour while being heated at 90° C., whereby particles of copper(I) oxide and copper (II) oxide were precipitated on the surfaces of the particles of titanium oxide.

Next, the particles after the reaction were filtrated, then subjected to sufficient water washing, and the particles were dried at 100° C. Consequently, a Cu$_x$O-supporting TiO$_2$ powder (co-catalyst-supporting type photocatalyst) was produced. According to the result of ICP analysis, it was confirmed that 1.0 part by weight of particles of copper oxide were supported with respect to 100 parts by weight of particles of titanium oxide. By the above-described method, an appropriate amount of Cu$_x$O-supporting TiO$_2$ powder to be incorporated into the epoxy resin cured body.

Then, 670 g of the Cu$_x$O-supporting TiO$_2$ powder produced above, a bisphenol A epoxy resin (jER 828: 2 kg, Mitsubishi Chemical Corporation), 450 g of 4,4'-methylenebis(cyclohexylamine), and 4.5 kg of polyethylene glycol (PEG 200, Sanyo Chemical Industries, Ltd.) were charged into a 15-liter SUS cylindrical container after applying a release agent inside the container. These were mixed and stirred, and cured at 100° C. for 12 hours to obtain an epoxy resin cured body. The cured body was then cut into a sheet of about a 100 μm thickness with a cutting lathe, and was dried after removing the polyethylene glycol in purified water, thereby obtaining a photocatalyst-containing epoxy resin porous sheet having a thickness of 88 and an average pore size of 600 nm. The photocatalyst-containing epoxy resin porous sheet was then cut into a photocatalyst-containing epoxy resin porous sheet measuring 15 cm in length and 10 cm in width (thickness 88 μm, average pore size 600 nm).

Figure 9:
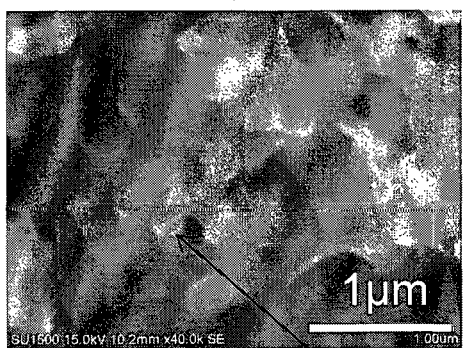
FIG. 9 shows SEM observation images of a surface of the epoxy resin porous sheet of Example 5.
Figure 9:
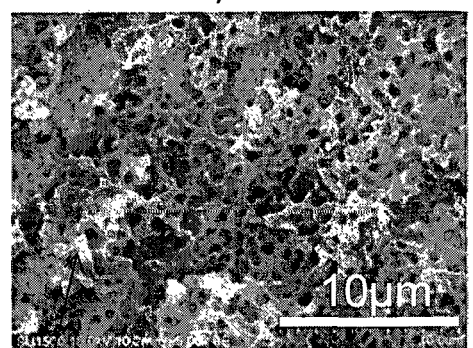

FIG. 9 shows SEM observation images of a surface of the photocatalyst-containing epoxy resin porous sheet of Example 5.

Example A

Porous Polyethersulfone (PES) Membrane with P-cat Loading

Polyethersulfone flake (10.0 gram) with average molecular weight of 50,000 and polydispersity index of about 3.4 was gradually added to a 200 mL glass jar containing 8.0 gram N-methyl-2-pyrrolidone (NMP) with continuous stirring until the PES appeared to have completely dissolved to make about 20 wt % of PES solution.

A plural phasic n-type semiconductor was loaded onto Cu$_x$O as described below. The weight fraction of copper to plural phasic n-type semiconductor (87% anatase phase $TiO_2$/13% rutile phase $TiO_2$ sold under the brandname "P25" [EvoniK Degussa, N.J., USA]) was about 0.01. Then, 15 mL aqueous solution of $CuCl_2 \cdot 2H_2O$ (26.8 mg) was stirred with 1 g of P25 at about 90° C. for 1 hr. Then, 1.5 mL of aqueous solution containing NaOH (25 mg) and glucose (125 mg) was added to the reaction mixture at about 90° C. while stirring. After the addition of aqueous solution of glucose and NaOH, the mixture was stirred for about another 1 h, then cooled down to room temperature, followed by filtration through 0.05 micron membrane, washing with 100 mL to 150 mL deionized (D.I.) water and finally dried it at 110° C. in air oven for about 2 hr.

Then, 0.2 g of the so made copper loaded titanium oxide particles with nominal copper content of 1 wt % was mixed with 4 mL N-methyl-2-pyrrolidone in 20 mL glass vial. Additional 20 µL surfactant solution comprising 1 wt % of G-700 (Kyoesha, Japan) in N-methyl-2-pyrrolidone was added into P-cat suspension. The mixture was dispersed by using a sonication horn (manufacturer, location) at an intensity level of about 4 to 8 for about 15 min, with the glass vial being chilled by ice to dissipate the heat generated by the sonication dispersion. The P-cat suspension treated with sonication horn was passed through a filter with stainless steel screen having an opening of 30 µm.

Filtered P-cat suspension was added to PES solution and mixed with planetary mixer (THINKY AR-310, JAPAN) for about 2 min at 2000 rpm and defoamed at 2200 rpm for about 1 min to get a homogeneous polymer solution. The viscosity of resulting polymer suspension was measured as about 50,000 mPa*s.

A polymer film was formed on glass plate by tape casting with a doctor blade with gap set at about 10 mil (1 mil equals to 1/1000 inch). The resulting cast polymer film was soaked in a coagulation bath containing D.I. water. The bath temperature was kept at about 25° C. An opaque porous film formed by keeping the cast film in coagulation bath for about 5 min. The porous film was then rinsed with D.I. water and dried at ambient atmosphere and temperature for overnight to get P-cat loaded porous PES membrane.

Highly porous films were formed, while not wanting to be bound by theory, it is believed, due in part, to the exchange of solvent in polymer solution and water. Pore size was in the range of 1 µm to 10 µm. All of pores were observed to be cylindrical and align in the direction perpendicular to the film surface. Also, P-cat particles were observed by SEM to distribute uniformly on the surface and pores without blocking the pores. The walls between the aligned pores were porous.

Example B

Antibacterial Activity
Photocatalytic Inactivation of *E. coli* (ATCC 8739)
Method:

Substrate (1 in×2 in glass slide) was prepared by sequential application of 70% isopropyl alcohol (IPA), 100% ethanol (EtOH) and then dried in air. The porous photocatalytic material synthesized as described in Example 1 above. The coated substrates were placed in a glass dish with a water soaked filter paper for maintaining moisture, and glass spacers were inserted between the substrate and the filter paper to separate them.

*E. coli* (ATCC 8739) was streaked onto a 10 cm diameter petri dish containing about 20 mL of LB (lysogeny broth/ luria broth) agar, and incubated at about 37° C. overnight. For each experiment, a single colony was picked to inoculate about 3 mL nutrient broth, and the inoculated culture was incubated at about 37° C. for about 16 hr to create an overnight culture (~$10^9$ cells/mL). A fresh log-phase culture of the overnight culture was obtained by diluting the overnight culture ×100, inoculating another 5 cm petri dish with LB agar and incubated about at 37° C. for about 2.5 hr. The fresh culture was diluted 50× with 0.85% saline, which will gave a cell suspension of about $2 \times 10^6$ cells/mL. 50 µL of the cell suspension was pipetted onto each deposited glass substrate. A sterilized (in 70% and then 100% EtOH) plastic film (20 mm×40 mm) was placed over the suspension to spread evenly under the film. The specimen was kept in the dark ($Cu_xO_2$-Dark) or then irradiated under blue LED light (455 nm, 10 mW/cm$^2$) ($CuO_2$-light). At chosen time point, e.g., 30 min/60 min increments, the specimen was placed in 10 mL of 0.85% saline and vortexed to wash off the bacteria. The wash off suspension was retained, then serially diluted using 0.85% saline, and then plated on LB agar and incubated at about 37° C. overnight to determine the number of viable cells in terms of CFU/Specimen.

Figure 8:
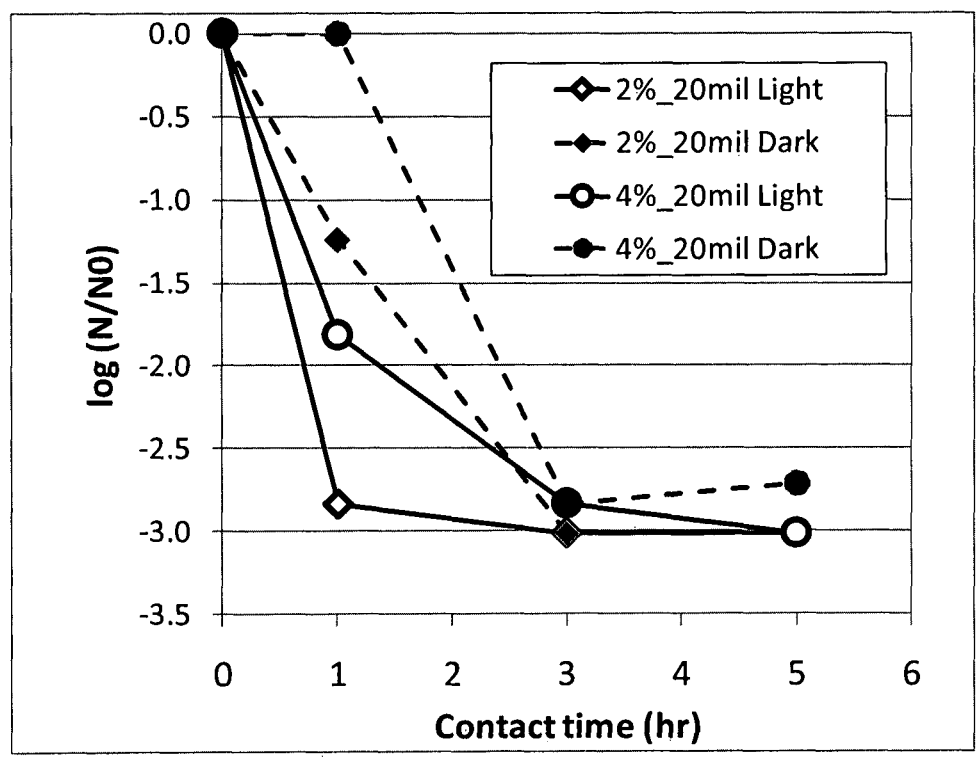
FIG. 8 is a graph of antibacterial (*E. Coli*) performance of Example A, as described in Example B.

The results are shown in FIG. 8. It appears that *E. coli* killing property due to presence of flexible copper ion was observed even in the dark within about 30 min. Therefore, it appears that the porous loaded material is a good functional material for *E. Coli* killing.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The present application is based on a U.S. provisional application No. 61/950,982 filed Mar. 11, 2014 and a Japanese patent application No. 2014-113002 filed May 30, 2014, the contents of which are incorporated herein by reference.

INDUSTRIAL APPLICABILITY

The photocatalytic element of the present invention has excellent antimicrobial effects, and can be used in a variety of applications where antimicrobial effects are desired. For example, the photocatalytic element of the present invention is useful for the prevention of mold generation, for example, in the cultivation, distribution, or preservation of plants, or in the distribution or preservation of food and beverages. The photocatalytic element of the present invention can also exhibit excellent antimicrobial effects when installed in spaces where antimicrobial effects are desired. The photocatalytic element of the present invention also has use, for example, in applications where photocatalytic activity is sought for air refreshment and deodorization purposes.

The invention claimed is:

1. A photocatalytic element comprising:
a porous resin sheet that comprises interconnecting pores, and a three-dimensional network skeleton forming the pores; and
a photocatalyst, wherein the photocatalyst satisfies at least one of the following: (1) it is supported on a surface of the three-dimensional network skeleton of the porous resin sheet and (2) it is contained in the three-dimensional network skeleton of the porous resin sheet;
and wherein the porous resin sheet contains a thermosetting resin.

2. The photocatalytic element according to claim 1, wherein the resin constituting the porous resin sheet contains an epoxy resin.

3. The photocatalytic element according to claim 1, wherein the photocatalyst shows a visible light responsiveness.

4. The photocatalytic element according to claim 1, further comprising a co-catalyst, wherein the co-catalyst satisfies at least one of the following: (1) it is supported on the surface of the three-dimensional network skeleton of the porous resin sheet and (2) it is contained in the three-dimensional network skeleton of the porous resin sheet.

5. The photocatalytic element according to claim 4, wherein the photocatalyst contains titanium(IV) oxide or tin(IV) oxide, and the co-catalyst contains copper(I) oxide, copper(II) oxide, or a combination thereof, and wherein the co-catalyst is supported on the photocatalyst.

6. The photocatalytic element according to claim 4, wherein the photocatalyst contains tungsten(VI) oxide, and the co-catalyst contains cerium(IV) oxide.

7. The photocatalytic element according to claim 1, wherein a photocatalyst layer containing the photocatalyst, or a photocatalyst layer containing the photocatalyst and the co-catalyst is formed on the surface of the three-dimensional network skeleton of the porous resin sheet.

8. The photocatalytic element according to claim 1, wherein the photocatalyst, or the photocatalyst and the co-catalyst are supported on the surface of the three-dimensional network skeleton of the porous resin through an aerosol deposition method.

9. The photocatalytic element according to claim 1, wherein the photocatalyst element has a form of a sheet.

10. A method for manufacturing the photocatalytic element according to claim 1, the method comprising:
dissolving a polymer in a first organic solvent to create a polymer precursor solution, wherein the polymer concentration is between 5% to 40% by weight;
dispersing a photocatalytic material in a second organic solvent to create a photocatalytic material suspension;
mixing the polymer solution with the photocatalytic suspension to create a photocatalytic polymer suspension; and
submerging the photocatalytic polymer suspension in a third solvent, the polymer substantially insoluble in the third solvent at a temperature between 10° C. to 60° C., creating the photocatalytic element.

11. The method according to claim 10, wherein the polymer is selected from polyethersulfone, polyacrylonitrile, polysulfone, and polypropylene.

12. The method according to claim 10, wherein the first organic solvent is selected from the group consisting of N-methyl-2-pyrrolidone (NMP), dimethyl formamide (DMF), dimethylacetamide (DMAC), dimethyl sulfoxide (DMSO), tetrahydrofuran (THF) and chloroform.

13. The method according to claim 10, wherein the second organic solvent is selected from the group consisting of N-methyl-2-pyrrolidone (NMP), dimethyl formamide (DMF), dimethylacetamide (DMAC), dimethyl sulfoxide (DMSO), tetrahydrofuran (THF) and chloroform.

14. The method according to claim 10, wherein the first and second organic solvent are the same.

15. The method according to claim 10, further comprising casting the photocatalytic polymer suspension on a substrate surface.

16. The method according to claim 10, further comprising filtering the photocatalytic suspension.

17. The method according to claim 10, wherein the third solvent is water.

18. The method according to claim 10, wherein the photocatalytic element is a porous photocatalytic film.

* * * * *